(12) United States Patent
Bonutti et al.

(10) Patent No.: US 11,801,044 B2
(45) Date of Patent: *Oct. 31, 2023

(54) TISSUE FIXATION SYSTEM AND METHOD

(71) Applicant: P Tech, LLC, Effingham, IL (US)

(72) Inventors: Peter M. Bonutti, Manalapan, FL (US); Hank Bonutti, Bloomfield Hills, MI (US); Kevin Ruholl, Teutopolis, IL (US); Glen A. Phillips, Effingham, IL (US)

(73) Assignee: P TECH, LLC, Manalapan, FL (US)

( * ) Notice: Subject to any disclaimer, the term of this patent is extended or adjusted under 35 U.S.C. 154(b) by 890 days.

This patent is subject to a terminal disclaimer.

(21) Appl. No.: 16/730,398

(22) Filed: Dec. 30, 2019

(65) Prior Publication Data

US 2020/0146674 A1  May 14, 2020

Related U.S. Application Data

(63) Continuation of application No. 16/551,471, filed on Aug. 26, 2019, now Pat. No. 10,517,584, which is a
(Continued)

(51) Int. Cl.
*A61B 17/04* (2006.01)
*A61B 17/68* (2006.01)
(Continued)

(52) U.S. Cl.
CPC ...... *A61B 17/0469* (2013.01); *A61B 17/0401* (2013.01); *A61B 17/683* (2013.01);
(Continued)

(58) Field of Classification Search
CPC ............ A61B 17/0482; A61B 17/3417; A61B 17/3421; A61B 2017/00637
See application file for complete search history.

(56) References Cited

U.S. PATENT DOCUMENTS 319,296 A    6/1885  Molesworth
668,878 A    2/1901  Jensen
(Continued)

FOREIGN PATENT DOCUMENTS

CA    2641580    8/2007
CA    2680827    9/2008
(Continued)

OTHER PUBLICATIONS

Petition for Inter Partes Review of U.S. Pat. No. 5,980,559, IPR 2013-00603, Filing Date Sep. 24, 2013.
(Continued)

*Primary Examiner* — Phong Son H Dang
(74) *Attorney, Agent, or Firm* — Stinson LLP

(57) ABSTRACT

A tissue fixation system is provided for dynamic and rigid fixation of tissue. A fastener connected with an elongate fastening member, such as a cable, wire, suture, rod, or tube, is moved through a passage between opposite sides of tissue. A medical device is used to secure the fastener to the elongate fastening member. The medical device includes a tensioning mechanism for tensioning the elongate fastening member. As crimping mechanism is used to secure the fastener to the elongated member, where a cutting mechanism cut the excess portion of the elongated member.

20 Claims, 30 Drawing Sheets

Related U.S. Application Data continuation of application No. 15/198,151, filed on Jun. 30, 2016, now Pat. No. 10,390,817, which is a continuation of application No. 14/096,859, filed on Dec. 4, 2013, now Pat. No. 9,402,668, which is a continuation of application No. 12/030,728, filed on Feb. 13, 2008, now Pat. No. 8,617,185.

(60) Provisional application No. 60/889,605, filed on Feb. 13, 2007.

(51) Int. Cl.
    *A61B 17/88*     (2006.01)
    *A61B 17/82*     (2006.01)
    *A61B 17/00*     (2006.01)
    *A61B 90/00*     (2016.01)
    *A61F 2/08*     (2006.01)

(52) U.S. Cl.
    CPC .......... *A61B 17/82* (2013.01); *A61B 17/8869* (2013.01); *A61B 2017/00893* (2013.01); *A61B 2017/0417* (2013.01); *A61B 2017/0462* (2013.01); *A61B 2017/0496* (2013.01); *A61B 2090/064* (2016.02); *A61F 2002/0882* (2013.01)

(56) References Cited

U.S. PATENT DOCUMENTS

| | | |
|---|---|---|
| 668,879 A | 2/1901 | Miller |
| 702,789 A | 6/1902 | Gibson |
| 862,712 A | 8/1907 | Collins |
| 2,121,193 A | 12/1932 | Hanicke |
| 2,187,852 A | 8/1936 | Friddle |
| 2,178,840 A | 11/1939 | Lorenian |
| 2,199,025 A | 4/1940 | Conn |
| 2,235,419 A | 3/1941 | Callahan |
| 2,248,054 A | 7/1941 | Becker |
| 2,270,188 A | 1/1942 | Longfellow |
| 2,485,531 A | 10/1949 | Dzus |
| 2,518,276 A | 8/1950 | Braward |
| 2,557,669 A | 6/1951 | Lloyd |
| 2,566,499 A | 9/1951 | Richter |
| 2,621,653 A | 12/1952 | Briggs |
| 2,725,053 A | 11/1955 | Bambara |
| 2,830,587 A | 4/1958 | Everett |
| 3,204,635 A | 9/1965 | Voss |
| 3,347,234 A | 10/1967 | Voss |
| 3,367,809 A | 2/1968 | Soloff |
| 3,391,690 A | 7/1968 | Armao |
| 3,477,429 A | 11/1969 | Sampson |
| 3,513,848 A | 5/1970 | Winston |
| 3,518,993 A | 7/1970 | Blake |
| 3,577,991 A | 5/1971 | Wilkinson |
| 3,596,292 A | 8/1971 | Erb |
| 3,608,539 A | 9/1971 | Miller |
| 3,625,220 A | 12/1971 | Engelsher |
| 3,648,705 A | 3/1972 | Lary |
| 3,653,388 A | 4/1972 | Tenckhoff |
| 3,656,476 A | 4/1972 | Swinney |
| 3,657,056 A | 4/1972 | Winston |
| 3,678,980 A | 7/1972 | Guttshall |
| 3,709,218 A | 1/1973 | Halloran |
| 3,711,347 A | 1/1973 | Wagner |
| 3,760,808 A | 9/1973 | Bleuer |
| 3,788,318 A | 1/1974 | Kim |
| 3,789,852 A | 2/1974 | Kim |
| 3,802,438 A | 4/1974 | Wolvek |
| 3,807,394 A | 4/1974 | Attenborough |
| 3,809,075 A | 5/1974 | Matles |
| 3,811,449 A | 5/1974 | Gravlee |
| 3,825,010 A | 7/1974 | McDonald |
| 3,833,003 A | 9/1974 | Taricco |
| 3,835,849 A | 9/1974 | McGuire |
| 3,842,824 A | 10/1974 | Neufeld |
| 3,857,396 A | 12/1974 | Hardwick |
| 3,867,932 A | 2/1975 | Huene |
| 3,875,652 A | 4/1975 | Arnold |
| 3,898,992 A | 8/1975 | Balamuth |
| 3,918,442 A | 11/1975 | Nikolaev |
| 3,959,960 A * | 6/1976 | Santos ............... A61B 17/8861 57/22 |
| 3,968,800 A | 7/1976 | Vilasi |
| 3,976,079 A | 8/1976 | Samuels |
| 4,023,559 A | 5/1977 | Gaskell |
| 4,064,566 A | 12/1977 | Fletcher |
| 4,089,071 A | 5/1978 | Kainberz |
| 4,108,399 A | 8/1978 | Pilgram |
| 4,156,574 A | 5/1979 | Boben |
| 4,164,794 A | 8/1979 | Spector |
| 4,171,544 A | 10/1979 | Hench |
| 4,183,102 A | 1/1980 | Guiset |
| 4,199,864 A | 4/1980 | Ashman |
| 4,200,939 A | 5/1980 | Oser |
| 4,210,148 A | 7/1980 | Stivala |
| 4,213,816 A | 7/1980 | Morris |
| 4,235,233 A | 11/1980 | Mouwen |
| 4,235,238 A | 11/1980 | Ogui |
| 4,257,411 A | 3/1981 | Cho |
| 4,265,231 A | 5/1981 | Scheller |
| 4,281,649 A | 8/1981 | Derweduwen |
| 4,291,698 A | 9/1981 | Fuchs |
| 4,309,488 A | 1/1982 | Heide |
| 4,320,762 A | 3/1982 | Bentov |
| 4,351,069 A | 9/1982 | Ballintyn |
| 4,364,381 A | 12/1982 | Sher |
| 4,365,356 A | 12/1982 | Broemer |
| 4,388,921 A | 6/1983 | Sutter |
| 4,395,798 A | 8/1983 | McVey |
| 4,409,974 A | 10/1983 | Freedland |
| 4,414,166 A | 11/1983 | Charlson |
| 4,437,191 A | 3/1984 | Van der Zat |
| 4,437,362 A | 3/1984 | Hurst |
| 4,444,180 A | 4/1984 | Schneider |
| 4,448,194 A | 5/1984 | DiGiovanni |
| 4,456,005 A | 6/1984 | Lichty |
| 4,461,281 A | 7/1984 | Carson |
| 4,471,777 A | 9/1984 | McCorkle, Jr. |
| 4,473,073 A | 9/1984 | Darnell |
| 4,493,317 A | 1/1985 | Klaue |
| 4,495,664 A | 1/1985 | Bianquaert |
| 4,501,031 A | 2/1985 | McDaniel |
| 4,504,268 A | 3/1985 | Herlitze |
| 4,506,681 A | 3/1985 | Mundell |
| 4,514,125 A | 4/1985 | Stol |
| 4,526,173 A | 7/1985 | Sheehan |
| 4,532,926 A | 8/1985 | O'Holla |
| 4,535,772 A | 8/1985 | Sheehan |
| 4,547,327 A | 10/1985 | Bruins |
| 4,556,350 A | 12/1985 | Bernhardt |
| 4,566,138 A | 1/1986 | Lewis |
| 4,589,868 A | 5/1986 | Dretler |
| 4,590,928 A | 5/1986 | Hunt |
| 4,597,379 A | 7/1986 | Kihn |
| 4,599,085 A | 7/1986 | Riess |
| 4,601,893 A | 7/1986 | Cardinal |
| 4,606,335 A | 8/1986 | Wedeen |
| 4,621,640 A | 11/1986 | Mulhollan |
| 4,630,609 A | 12/1986 | Chin |
| 4,632,100 A | 12/1986 | Somers |
| 4,632,101 A | 12/1986 | Freedland |
| 4,645,503 A | 2/1987 | Lin |
| 4,657,460 A | 4/1987 | Bien |
| 4,659,268 A | 4/1987 | Del Mundo |
| 4,662,063 A | 5/1987 | Collins |
| 4,662,068 A | 5/1987 | Polonsky |
| 4,662,887 A | 5/1987 | Turner |
| 4,669,473 A | 6/1987 | Richards |
| 4,685,458 A | 8/1987 | Leckrone |
| 4,688,561 A | 8/1987 | Reese |
| 4,691,741 A | 9/1987 | Affa |
| 4,705,040 A | 11/1987 | Mueller |
| 4,706,670 A | 11/1987 | Andersen |

(56) References Cited

U.S. PATENT DOCUMENTS

| | | |
|---|---|---|
| 4,708,139 A | 11/1987 | Dunbar |
| 4,713,077 A | 12/1987 | Small |
| 4,716,901 A | 1/1988 | Jackson |
| 4,718,909 A | 1/1988 | Brown |
| 4,722,331 A | 2/1988 | Fox |
| 4,722,948 A | 2/1988 | Sanderson |
| 4,724,584 A | 2/1988 | Kasai |
| 4,738,255 A | 4/1988 | Goble |
| 4,739,751 A | 4/1988 | Sapega |
| 4,741,330 A | 5/1988 | Hayhurst |
| 4,743,257 A | 5/1988 | Tormala |
| 4,749,585 A | 6/1988 | Greco |
| 4,750,492 A | 6/1988 | Jacobs |
| 4,769,507 A | 9/1988 | Fischell |
| 4,772,286 A | 9/1988 | Goble |
| 4,776,328 A | 10/1988 | Frey |
| 4,776,738 A | 10/1988 | Winston |
| 4,776,851 A | 10/1988 | Bruchman |
| 4,781,182 A | 11/1988 | Purnell |
| 4,790,303 A | 12/1988 | Steflee |
| 4,792,336 A | 12/1988 | Hiavacek |
| 4,796,612 A | 1/1989 | Reese |
| 4,817,591 A | 4/1989 | Klaue |
| 4,822,224 A | 4/1989 | Carl |
| 4,823,794 A | 4/1989 | Pierce |
| 4,832,025 A | 5/1989 | Coates |
| 4,832,026 A | 5/1989 | Jones |
| 4,834,752 A | 5/1989 | Van Kampen |
| 4,841,960 A | 6/1989 | Garner |
| 4,843,112 A | 6/1989 | Gerhart |
| 4,846,812 A | 7/1989 | Walker |
| 4,862,882 A | 9/1989 | Venturi |
| 4,869,242 A | 9/1989 | Galluzzo |
| 4,870,957 A | 10/1989 | Goble |
| 4,883,048 A | 11/1989 | Purnell |
| 4,890,612 A | 1/1990 | Kensey |
| 4,895,148 A | 1/1990 | Bays |
| 4,898,156 A | 2/1990 | Gatturna |
| 4,899,729 A | 2/1990 | Gill |
| 4,899,744 A | 2/1990 | Fujitsuka |
| 4,901,721 A | 2/1990 | Hakki |
| 4,921,479 A | 5/1990 | Grayzel |
| 4,922,897 A | 5/1990 | Sapega |
| 4,924,866 A | 5/1990 | Yoon |
| 4,932,960 A | 6/1990 | Green |
| 4,935,026 A | 6/1990 | Drews |
| 4,935,027 A | 6/1990 | Yoon |
| 4,935,028 A | 6/1990 | Drews |
| 4,945,625 A | 8/1990 | Winston |
| 4,946,468 A | 8/1990 | Li |
| 4,950,285 A | 8/1990 | Wilk |
| 4,954,126 A | 9/1990 | Wallsten |
| 4,955,910 A | 9/1990 | Bolesky |
| 4,957,498 A | 9/1990 | Caspari |
| 4,961,741 A | 10/1990 | Hayhurst |
| 4,963,151 A | 10/1990 | Ducheyne |
| 4,968,315 A | 11/1990 | Gatturna |
| 4,968,317 A | 11/1990 | Tormala |
| 4,969,888 A | 11/1990 | Scholten |
| 4,969,892 A | 11/1990 | Burton |
| 4,990,161 A | 2/1991 | Kampner |
| 4,994,071 A | 2/1991 | MacGregor |
| 4,996,583 A | 2/1991 | Hatada |
| 4,997,445 A | 3/1991 | Hodorek |
| 4,998,539 A | 3/1991 | Delsanti |
| 5,002,550 A | 3/1991 | Li |
| 5,002,563 A | 3/1991 | Pyka |
| 5,009,652 A | 4/1991 | Morgan |
| 5,009,663 A | 4/1991 | Broome |
| 5,009,664 A | 4/1991 | Sievers |
| 5,013,316 A | 5/1991 | Goble |
| 5,019,090 A | 5/1991 | Pinchuk |
| 5,021,059 A | 6/1991 | Kensey |
| 5,035,713 A | 7/1991 | Friis |
| 5,037,404 A | 8/1991 | Gold |
| 5,037,422 A | 8/1991 | Hayhurst |
| 5,041,093 A | 8/1991 | Chu |
| 5,041,114 A | 8/1991 | Chapman |
| 5,041,129 A | 8/1991 | Hayhurst |
| 5,046,513 A | 9/1991 | Gatturna |
| 5,047,055 A | 9/1991 | Bao |
| 5,051,049 A | 9/1991 | Wills |
| 5,053,046 A | 10/1991 | Janese |
| 5,053,047 A | 10/1991 | Yoon |
| 5,059,193 A | 10/1991 | Kuslich |
| 5,059,206 A | 10/1991 | Winters |
| 5,061,274 A | 10/1991 | Kensey |
| 5,061,286 A | 10/1991 | Lyle |
| 5,069,674 A | 12/1991 | Fearnot |
| 5,078,731 A | 1/1992 | Hayhurst |
| 5,078,744 A | 1/1992 | Chvapil |
| 5,078,745 A | 1/1992 | Rhenter |
| 5,084,050 A | 1/1992 | Draenert |
| 5,084,051 A | 1/1992 | Tormala |
| 5,085,660 A | 2/1992 | Lin |
| 5,085,661 A | 2/1992 | Moss |
| 5,098,433 A | 3/1992 | Freedland |
| 5,098,434 A | 3/1992 | Serbousek |
| 5,098,436 A | 3/1992 | Ferrante |
| 5,100,405 A | 3/1992 | McLaren |
| 5,100,417 A | 3/1992 | Cerier |
| 5,102,417 A | 4/1992 | Palmaz |
| 5,102,421 A | 4/1992 | Anspach |
| 5,120,175 A | 6/1992 | Arbegast |
| 5,123,520 A | 6/1992 | Schmid |
| 5,123,914 A | 6/1992 | Cope |
| 5,123,941 A | 6/1992 | Lauren |
| 5,133,732 A | 7/1992 | Wiktor |
| RE34,021 E | 8/1992 | Mueller |
| 5,141,520 A | 8/1992 | Goble |
| 5,147,362 A | 9/1992 | Goble |
| 5,154,720 A | 10/1992 | Trott |
| 5,156,613 A | 10/1992 | Sawyer |
| 5,156,616 A | 10/1992 | Meadows |
| 5,158,566 A | 10/1992 | Pianetti |
| 5,158,934 A | 10/1992 | Ammann |
| 5,163,960 A | 11/1992 | Bonutti |
| 5,171,251 A | 12/1992 | Bregen |
| 5,176,682 A | 1/1993 | Chow |
| 5,179,964 A | 1/1993 | Cook |
| 5,180,385 A | 1/1993 | Sontag |
| 5,180,388 A | 1/1993 | DiCarlo |
| 5,183,464 A | 2/1993 | Dubrul |
| 5,192,287 A | 3/1993 | Fournier |
| 5,192,326 A | 3/1993 | Bao |
| 5,197,166 A | 3/1993 | Meier |
| 5,197,971 A | 3/1993 | Bonutti |
| 5,203,784 A | 4/1993 | Ross |
| 5,203,787 A | 4/1993 | Noblitt |
| 5,208,950 A | 5/1993 | Merritt |
| 5,209,776 A | 5/1993 | Bass |
| 5,217,493 A | 6/1993 | Raad |
| 5,219,359 A | 6/1993 | McQuilkin |
| 5,226,899 A | 7/1993 | Lee |
| 5,234,006 A | 8/1993 | Eaton |
| 5,234,425 A | 8/1993 | Fogarty |
| 5,234,443 A | 8/1993 | Phan |
| 5,236,438 A | 8/1993 | Wilk |
| 5,236,445 A | 8/1993 | Hayhurst |
| 5,242,902 A | 9/1993 | Murphy |
| 5,250,049 A | 10/1993 | Michael |
| 5,254,113 A | 10/1993 | Wilk |
| 5,258,007 A | 11/1993 | Spetzler |
| 5,258,015 A | 11/1993 | Li |
| 5,258,016 A | 11/1993 | DiPoto |
| 5,261,886 A | 11/1993 | Chesterfield |
| 5,266,325 A | 11/1993 | Kuzma |
| 5,269,783 A | 12/1993 | Sander |
| 5,269,785 A | 12/1993 | Bonutti |
| 5,269,809 A | 12/1993 | Hayhurst |
| 5,281,235 A | 1/1994 | Haber |
| 5,282,832 A | 2/1994 | Toso |
| 5,290,281 A | 3/1994 | Tschakaloff |
| 5,304,119 A | 4/1994 | Balaban |

(56) References Cited

U.S. PATENT DOCUMENTS

| | | |
|---|---|---|
| 5,306,280 A | 4/1994 | Bregen |
| 5,306,301 A | 4/1994 | Graf |
| 5,312,410 A | 5/1994 | Miller |
| 5,315,741 A | 5/1994 | Dubberke |
| 5,318,588 A | 6/1994 | Horzewski |
| 5,320,611 A | 6/1994 | Bonutti |
| 5,322,064 A | 6/1994 | Lundquist |
| 5,324,308 A | 6/1994 | Pierce |
| 5,328,480 A | 7/1994 | Melker |
| 5,329,846 A | 7/1994 | Bonutti |
| 5,329,924 A | 7/1994 | Bonutti |
| 5,330,468 A | 7/1994 | Burkhart |
| 5,330,476 A | 7/1994 | Hiot |
| 5,330,486 A | 7/1994 | WIlk |
| 5,336,231 A | 8/1994 | Adair |
| 5,336,240 A | 8/1994 | Metzler |
| 5,339,799 A | 8/1994 | Kami |
| 5,349,956 A | 9/1994 | Bonutti |
| 5,352,229 A | 10/1994 | Goble |
| 5,354,298 A | 10/1994 | Lee |
| 5,354,302 A | 10/1994 | Ko |
| 5,366,480 A | 11/1994 | Corriveaau |
| 5,370,646 A | 12/1994 | Reese |
| 5,370,660 A | 12/1994 | Weinstein |
| 5,372,146 A | 12/1994 | Branch |
| 5,374,235 A | 12/1994 | Ahrens |
| 5,376,126 A | 12/1994 | Lin |
| 5,382,254 A | 1/1995 | McGarry |
| 5,383,883 A | 1/1995 | Wilk |
| 5,383,905 A | 1/1995 | Golds |
| 5,391,173 A | 2/1995 | Wilk |
| 5,395,308 A | 3/1995 | Fox |
| 5,397,311 A | 3/1995 | Wlaker |
| 5,400,805 A | 3/1995 | Warren |
| 5,403,312 A | 4/1995 | Fates |
| 5,403,348 A | 4/1995 | Bonutti |
| 5,405,359 A | 4/1995 | Pierce |
| 5,411,523 A | 5/1995 | Goble |
| 5,413,585 A | 5/1995 | Pagedas |
| 5,417,691 A | 5/1995 | Hayhurst |
| 5,417,701 A | 5/1995 | Holmes |
| 5,417,712 A | 5/1995 | Whittaker |
| 5,423,796 A | 6/1995 | Shikhman |
| 5,431,670 A | 7/1995 | Holmes |
| 5,439,470 A | 8/1995 | Li |
| 5,441,538 A | 8/1995 | Bonutti |
| 5,443,512 A | 8/1995 | Parr |
| 5,447,503 A | 9/1995 | Miller |
| 5,449,372 A | 9/1995 | Schmaltz |
| 5,449,382 A | 9/1995 | Dayton |
| 5,451,235 A | 9/1995 | Lock |
| 5,453,090 A | 9/1995 | Martinez |
| 5,456,722 A | 10/1995 | McLeod |
| 5,458,653 A | 10/1995 | Davison |
| 5,462,561 A | 10/1995 | Voda |
| 5,464,424 A | 11/1995 | O'Donell |
| 5,464,426 A | 11/1995 | Bonutti |
| 5,464,427 A | 11/1995 | Curtis |
| 5,470,337 A | 11/1995 | Moss |
| 5,472,444 A | 12/1995 | Huebner |
| 5,474,554 A | 12/1995 | Ku |
| 5,478,351 A | 12/1995 | Meade |
| 5,478,353 A | 12/1995 | Yoon |
| 5,480,403 A | 1/1996 | Lee |
| 5,486,197 A | 1/1996 | Le |
| 5,487,844 A | 1/1996 | Fujita |
| 5,488,958 A | 2/1996 | Topel |
| 5,496,292 A | 3/1996 | Burnham |
| 5,496,318 A | 3/1996 | Howland |
| 5,496,335 A | 3/1996 | Thomason |
| 5,496,348 A | 3/1996 | Bonutti |
| 5,500,000 A | 3/1996 | Feagin |
| 5,501,700 A | 3/1996 | Hirata |
| 5,504,977 A | 4/1996 | Weppner |
| 5,505,735 A | 4/1996 | Li |
| 5,507,754 A | 4/1996 | Green |
| 5,522,844 A | 6/1996 | Johnson |
| 5,522,845 A | 6/1996 | WEnstrom |
| 5,522,846 A | 6/1996 | Bonutti |
| 5,527,341 A | 6/1996 | Gogolewski |
| 5,527,342 A | 6/1996 | Pietrzak |
| 5,527,343 A | 6/1996 | Bonutti |
| 5,529,075 A | 6/1996 | Clark |
| 5,531,759 A | 7/1996 | Kensey |
| 5,534,012 A | 7/1996 | Bonutti |
| 5,534,028 A | 7/1996 | Bao |
| 5,540,718 A | 7/1996 | Bartlett |
| 5,542,423 A | 8/1996 | Bonutti |
| 5,545,178 A | 8/1996 | Kensey |
| 5,545,180 A | 8/1996 | Le |
| 5,545,206 A | 8/1996 | Carson |
| 5,549,630 A | 8/1996 | Bonutti |
| 5,549,631 A | 8/1996 | Bonutti |
| 5,556,402 A | 9/1996 | Xu |
| 5,569,252 A | 10/1996 | Justin |
| 5,569,305 A | 10/1996 | Bonutti |
| 5,569,306 A | 10/1996 | Thal |
| 5,573,517 A | 11/1996 | Bonutti |
| 5,573,538 A | 11/1996 | Laboureau |
| 5,573,542 A | 11/1996 | Stevens |
| 5,575,801 A | 11/1996 | Habermeyer |
| 5,578,046 A | 11/1996 | Liu |
| 5,580,344 A | 12/1996 | Hasson |
| 5,584,835 A | 12/1996 | Greenfield |
| 5,584,839 A | 12/1996 | Gieringer |
| 5,584,860 A | 12/1996 | Goble |
| 5,584,862 A | 12/1996 | Bonutti |
| 5,591,206 A | 1/1997 | Moufarrege |
| 5,593,422 A | 1/1997 | Muijs Van De Moer |
| 5,593,425 A | 1/1997 | Bonutti |
| 5,593,625 A | 1/1997 | Riebel |
| 5,601,557 A | 2/1997 | Hayhurst |
| 5,601,558 A | 2/1997 | Torrie |
| 5,601,595 A | 2/1997 | Schwartz |
| 5,607,427 A | 3/1997 | Tschakaloff |
| 5,609,595 A | 3/1997 | Pennig |
| 5,618,314 A | 4/1997 | Idarwin |
| 5,620,461 A | 4/1997 | Muijs Van De Moer |
| 5,626,612 A | 5/1997 | Bartlett |
| 5,626,614 A | 5/1997 | Hart |
| 5,626,718 A | 5/1997 | Philippe |
| 5,630,824 A | 5/1997 | Hart |
| 5,634,926 A | 6/1997 | Jobe |
| 5,628,751 A | 7/1997 | Sander |
| 5,643,274 A | 7/1997 | Sander |
| 5,643,289 A | 7/1997 | Sauer |
| 5,643,293 A | 7/1997 | Kogasaka |
| 5,643,295 A | 7/1997 | Yoon |
| 5,643,321 A | 7/1997 | McDevitt |
| 5,645,553 A | 7/1997 | Kolesa |
| 5,645,597 A | 7/1997 | Krapiva |
| 5,645,599 A | 7/1997 | Samani |
| 5,649,955 A | 7/1997 | Hashimoto |
| 5,649,963 A | 7/1997 | McDevitt |
| 5,651,377 A | 7/1997 | O'Donnell |
| 5,658,313 A | 8/1997 | Thal |
| 5,660,225 A | 8/1997 | Saffran |
| 5,662,658 A | 9/1997 | Wenstrom |
| 5,665,089 A | 9/1997 | Dall |
| 5,665,109 A | 9/1997 | Yoon |
| 5,667,513 A | 9/1997 | Torrie |
| 5,669,917 A | 9/1997 | Sauer |
| 5,674,240 A | 10/1997 | Bonutti |
| 5,681,310 A | 10/1997 | Yuan |
| 5,681,333 A | 10/1997 | Burkhart |
| 5,681,351 A | 10/1997 | Jamiolkowski |
| 5,681,352 A | 10/1997 | Clancy |
| 5,685,820 A | 11/1997 | Riek |
| 5,688,283 A | 11/1997 | Knapp |
| 5,690,654 A | 11/1997 | Ovil |
| 5,690,655 A | 11/1997 | Hart |
| 5,690,676 A | 11/1997 | DiPoto |
| 5,693,055 A | 12/1997 | Zahiri |
| 5,697,950 A | 12/1997 | Fucci |

(56) References Cited

U.S. PATENT DOCUMENTS

| | | | |
|---|---|---|---|
| 5,702,397 | A | 12/1997 | Gonle |
| 5,702,462 | A | 12/1997 | Oberlander |
| 5,707,395 | A | 1/1998 | Li |
| 5,713,903 | A | 2/1998 | Sander |
| 5,713,921 | A | 2/1998 | Bonutti |
| 5,718,717 | A | 2/1998 | Bonutti |
| 5,720,747 | A | 2/1998 | Burke |
| 5,725,541 | A | 3/1998 | Anspach |
| 5,725,556 | A | 3/1998 | Moser |
| 5,725,582 | A | 3/1998 | Bevan |
| 5,727,547 | A * | 3/1998 | Levinson ............ A61B 5/1464 600/338 |
| 5,730,747 | A | 3/1998 | Ek |
| 5,733,306 | A | 3/1998 | Bonutti |
| 5,720,753 | A | 4/1998 | Sander |
| 5,735,875 | A | 4/1998 | Bonutti |
| 5,735,877 | A | 4/1998 | Pagedas |
| 5,735,899 | A | 4/1998 | Schwartz |
| 5,741,282 | A | 4/1998 | Anspach |
| 5,749,533 | A | 5/1998 | Daniels |
| 5,752,952 | A | 5/1998 | Adamson |
| 5,752,974 | A | 5/1998 | Rhee |
| 5,755,809 | A | 5/1998 | Cohen |
| 5,762,458 | A | 6/1998 | Wang |
| 5,766,221 | A | 6/1998 | Benderev |
| 5,769,894 | A | 6/1998 | Ferragamo |
| 5,772,672 | A | 6/1998 | Toy |
| 5,776,151 | A | 7/1998 | Chan |
| 5,779,706 | A | 7/1998 | Tschakaloff |
| 5,782,862 | A | 7/1998 | Bonutti |
| 5,785,713 | A | 7/1998 | Jobe |
| 5,788,697 | A | 8/1998 | Kilpela |
| 5,792,096 | A | 8/1998 | Rentmeester |
| 5,797,931 | A | 8/1998 | Bito |
| 5,800,537 | A | 9/1998 | Bell |
| 5,807,403 | A | 9/1998 | Beyar |
| 5,810,849 | A | 9/1998 | Kontos |
| 5,810,853 | A | 9/1998 | Yoon |
| 5,810,884 | A | 9/1998 | Kim |
| 5,814,052 | A | 9/1998 | Nakao et al. |
| 5,814,072 | A | 9/1998 | Bonutti |
| 5,814,073 | A | 9/1998 | Bonutti |
| 5,817,107 | A | 10/1998 | Schaller |
| 5,823,994 | A | 10/1998 | Sharkey |
| 5,824,009 | A | 10/1998 | Fukuda |
| 5,830,125 | A | 11/1998 | Scribner |
| 5,836,897 | A | 11/1998 | Sakural |
| 5,839,899 | A | 11/1998 | Robinson |
| 5,843,084 | A | 12/1998 | Hart |
| 5,843,178 | A | 12/1998 | Vanney |
| 5,845,645 | A | 12/1998 | Bonutti |
| 5,851,185 | A | 12/1998 | Berns |
| 5,865,834 | A | 2/1999 | McGuire |
| 5,866,634 | A | 2/1999 | Tokushige |
| 5,868,749 | A | 2/1999 | Reed |
| 5,874,235 | A | 2/1999 | CHan |
| 5,879,372 | A | 3/1999 | Bartlett |
| 5,891,166 | A | 4/1999 | Schervinsky |
| 5,891,168 | A | 4/1999 | Thal |
| 5,893,880 | A | 4/1999 | Egan |
| 5,897,574 | A | 4/1999 | Bonutti |
| 5,899,911 | A | 5/1999 | Carter |
| 5,899,921 | A | 5/1999 | Caspari |
| 5,902,321 | A * | 5/1999 | Caspari ............ A61B 17/0487 606/232 |
| 5,906,579 | A | 5/1999 | Salm |
| 5,906,625 | A | 5/1999 | Bito |
| 5,908,429 | A | 6/1999 | Yoon |
| 5,911,721 | A | 6/1999 | Nicholson |
| 5,918,604 | A | 7/1999 | Whelan |
| 5,919,193 | A | 7/1999 | Slavitt |
| 5,919,194 | A | 7/1999 | Anderson |
| 5,919,199 | A | 7/1999 | Mers Kelly et al. |
| 5,919,208 | A | 7/1999 | Vlaenti |
| 5,919,215 | A | 7/1999 | Wiklund |
| 5,921,986 | A | 7/1999 | Bonutti |
| 5,925,064 | A | 7/1999 | Meyers |
| 5,928,244 | A | 7/1999 | Tovey |
| 5,928,267 | A | 7/1999 | Bonutti |
| 5,931,838 | A | 8/1999 | Vito |
| 5,931,869 | A | 8/1999 | Boucher |
| 5,940,942 | A | 8/1999 | Fong |
| 5,941,900 | A | 8/1999 | Bonutti |
| 5,941,901 | A | 8/1999 | Egan |
| 5,944,750 | A | 8/1999 | Tanner |
| 5,945,002 | A | 9/1999 | Bonutti |
| 5,947,982 | A | 9/1999 | Duran |
| 5,948,000 | A | 9/1999 | Larsen |
| 5,948,001 | A | 9/1999 | Larsen |
| 5,948,002 | A | 9/1999 | Bonutti |
| 5,951,590 | A | 9/1999 | Goldfarb |
| 5,957,953 | A | 9/1999 | DiPoto |
| 5,961,499 | A | 10/1999 | Bonutti |
| 5,961,521 | A | 10/1999 | Roger |
| 5,961,554 | A | 10/1999 | Janson |
| 5,964,765 | A | 10/1999 | Fenton |
| 5,964,769 | A | 10/1999 | Wagner |
| 5,968,046 | A | 10/1999 | Castleman |
| 5,968,047 | A | 10/1999 | Reed |
| 5,980,520 | A | 11/1999 | Vancaillie |
| 5,980,559 | A | 11/1999 | Bonutti |
| 5,984,929 | A | 11/1999 | Bashiri |
| 5,989,282 | A | 11/1999 | Bonutti |
| 5,993,458 | A | 11/1999 | Vaitekunas |
| 5,993,477 | A | 11/1999 | Vaitekunas |
| 6,007,567 | A | 12/1999 | Bonutti |
| 6,007,580 | A | 12/1999 | Lehto |
| 6,010,525 | A | 1/2000 | Bonutti |
| 6,010,526 | A | 1/2000 | Sandstrom |
| 6,017,321 | A | 1/2000 | Boone |
| 6,033,429 | A | 3/2000 | Magovern |
| 6,033,430 | A | 3/2000 | Bonutti |
| 6,045,551 | A | 4/2000 | Bonutti |
| 6,050,937 | A * | 4/2000 | Benderev ............ A61B 90/06 600/30 |
| 6,050,998 | A | 4/2000 | Fletcher |
| 6,056,751 | A | 5/2000 | Fenton |
| 6,056,772 | A | 5/2000 | Bonutti |
| 6,056,773 | A | 5/2000 | Bonutti |
| 6,059,797 | A | 5/2000 | Mears |
| 6,059,817 | A | 5/2000 | Bonutti |
| 6,059,827 | A | 5/2000 | Fenton |
| 6,063,095 | A | 5/2000 | Wang |
| 6,066,151 | A | 5/2000 | Miyawaki |
| 6,066,160 | A | 5/2000 | Colvin |
| 6,066,166 | A | 5/2000 | Bischoff |
| 6,068,637 | A | 5/2000 | Popov |
| 6,068,648 | A | 5/2000 | Cole |
| 6,077,277 | A | 6/2000 | Mollenauer |
| 6,077,292 | A | 6/2000 | Mollenauer |
| 6,080,161 | A | 6/2000 | Eaves |
| 6,083,522 | A | 7/2000 | Chu |
| 6,086,593 | A | 7/2000 | Bonutti |
| 6,086,608 | A | 7/2000 | Ek |
| 6,090,072 | A | 8/2000 | Kratoska |
| 6,099,531 | A | 8/2000 | Bonutti |
| 6,099,537 | A | 8/2000 | Sugai |
| 6,099,550 | A | 8/2000 | Yoon |
| 6,099,552 | A | 8/2000 | Adams |
| 6,102,850 | A | 8/2000 | Wang |
| 6,106,545 | A | 8/2000 | Egan |
| 6,117,160 | A | 9/2000 | Bonutti |
| 6,120,536 | A | 9/2000 | Ding |
| 6,122,574 | A | 10/2000 | Ganaja |
| 6,126,677 | A | 10/2000 | Ganaja |
| 6,139,320 | A | 10/2000 | Hahn |
| RE36,974 | E | 11/2000 | Bonutti |
| 6,149,669 | A | 11/2000 | Li |
| 6,152,949 | A | 11/2000 | Bonutti |
| 6,155,756 | A | 12/2000 | Mericle |
| 6,159,224 | A | 12/2000 | Yoon |
| 6,159,234 | A | 12/2000 | Bonutti |
| 6,171,299 | B1 | 1/2001 | Bonutti |
| 6,171,307 | B1 | 1/2001 | Bonutti |

(56) References Cited

U.S. PATENT DOCUMENTS

| | | |
|---|---|---|
| 6,174,324 B1 | 1/2001 | Egan |
| 6,179,840 B1 | 1/2001 | Bowman |
| 6,179,850 B1 | 1/2001 | Goradia |
| 6,187,008 B1 | 2/2001 | Hamman |
| 6,190,400 B1 | 2/2001 | Van De Moer |
| 6,190,401 B1 | 2/2001 | Green |
| 6,200,322 B1 | 3/2001 | Branch |
| 6,200,329 B1 | 3/2001 | Fung |
| 6,217,591 B1 | 4/2001 | Egan |
| 6,224,593 B1 | 5/2001 | Ryan |
| 6,224,630 B1 | 5/2001 | Bao |
| 6,228,086 B1 | 5/2001 | Wahl |
| 6,231,592 B1 | 5/2001 | Bonutti |
| 6,238,395 B1 | 5/2001 | Bonutti |
| 6,238,396 B1 | 5/2001 | Bonutti |
| 6,258,091 B1 | 7/2001 | Sevrain |
| 6,264,675 B1 | 7/2001 | Brotz |
| 6,267,761 B1 | 7/2001 | Ryan |
| 6,273,717 B1 | 8/2001 | Hahn |
| 6,280,474 B1 | 8/2001 | Cassidy |
| 6,283,979 B1 * | 9/2001 | Mers Kelly ........ A61B 17/0469 606/139 |
| 6,286,746 B1 | 9/2001 | Egan |
| 6,287,325 B1 | 9/2001 | Bonutti |
| 6,293,961 B2 | 9/2001 | Schwartz |
| 6,302,840 B1 * | 10/2001 | Benderev ............. A61F 2/0036 600/37 |
| 6,306,159 B1 | 10/2001 | Schwartz |
| 6,309,405 B1 | 10/2001 | Bonutti |
| 6,312,448 B1 | 11/2001 | Bonutti |
| 6,338,730 B1 | 1/2002 | Bonutti |
| 6,340,365 B2 | 1/2002 | Dittrich |
| 6,348,056 B1 | 2/2002 | Bates |
| 6,358,271 B1 | 3/2002 | Egan |
| 6,364,885 B1 | 4/2002 | Kilpela |
| 6,364,897 B1 | 4/2002 | Bonutti |
| 6,368,325 B1 | 4/2002 | McKinley |
| 6,368,343 B1 | 4/2002 | Bonutti |
| 6,371,957 B1 | 4/2002 | Amrein |
| 6,409,742 B1 | 6/2002 | Fulton |
| 6,409,743 B1 | 6/2002 | Fenton |
| 6,419,704 B1 | 7/2002 | Ferree |
| 6,423,088 B1 | 7/2002 | Fenton |
| 6,425,919 B1 | 7/2002 | Lambrecht |
| 6,428,562 B2 | 8/2002 | Bonutti |
| 6,432,115 B1 | 8/2002 | Mollenauer |
| 6,447,516 B1 | 9/2002 | Bonutti |
| 6,450,985 B1 | 9/2002 | Scheolling |
| 6,461,360 B1 | 10/2002 | Adams |
| 6,468,293 B2 | 10/2002 | Bonutti |
| 6,475,230 B1 | 11/2002 | Bonutti |
| 6,488,196 B1 | 12/2002 | Fenton |
| 6,500,195 B2 | 12/2002 | Bonutti |
| 6,503,259 B2 | 1/2003 | Huxel |
| 6,527,774 B2 | 3/2003 | Lieberman |
| 6,530,933 B1 | 3/2003 | Yeung |
| 6,535,764 B2 | 3/2003 | Imran |
| 6,544,267 B1 | 4/2003 | Cole |
| 6,545,390 B1 | 4/2003 | Hahn |
| 6,547,792 B1 | 4/2003 | Tsuji |
| 6,551,304 B1 | 4/2003 | Whalen |
| 6,551,343 B1 | 4/2003 | Tormala |
| 6,554,852 B1 | 4/2003 | Oberlander |
| 6,557,426 B2 | 5/2003 | Reinemann |
| 6,558,390 B2 | 5/2003 | Cragg |
| 6,568,313 B2 | 5/2003 | Fukui |
| 6,569,187 B1 | 5/2003 | Bonutti |
| 6,572,635 B1 | 6/2003 | Bonutti |
| D477,776 S | 7/2003 | Pontaoe |
| 6,585,750 B2 | 7/2003 | Bonutti |
| 6,592,609 B1 | 7/2003 | Bonutti |
| 6,594,517 B1 | 7/2003 | Nevo |
| 6,595,994 B2 * | 7/2003 | Kilpela ............. A61B 17/8869 606/103 |
| 6,585,764 B2 | 8/2003 | Wright |
| 6,602,293 B1 | 8/2003 | Biermann |
| 6,605,090 B1 | 8/2003 | Trieu |
| 6,610,080 B2 | 8/2003 | Morgan |
| 6,618,910 B1 | 9/2003 | Pontaoe |
| 6,623,487 B1 | 9/2003 | Goshert |
| 6,626,944 B1 | 9/2003 | Taylor |
| 6,623,486 B1 | 10/2003 | Weaver |
| 6,632,245 B2 | 10/2003 | Kim |
| 6,635,073 B2 | 10/2003 | Bonutti |
| 6,638,279 B2 | 10/2003 | Bonutti |
| 6,641,592 B1 | 11/2003 | Sauer |
| 6,645,227 B2 | 11/2003 | Fallin |
| 6,666,877 B2 | 12/2003 | Morgan |
| 6,669,705 B2 | 12/2003 | Westhaver |
| 6,679,888 B2 | 1/2004 | Green |
| 6,685,750 B1 | 2/2004 | Plos |
| 6,699,240 B2 | 3/2004 | Fracischelli |
| 6,702,821 B2 | 3/2004 | Bonutti |
| 6,705,179 B1 | 3/2004 | Mohtasham |
| 6,709,457 B1 | 3/2004 | Otte |
| 6,719,765 B2 | 4/2004 | Bonutti |
| 6,719,795 B1 | 4/2004 | Cornwall |
| 6,719,797 B1 | 4/2004 | Ferree |
| 6,722,552 B2 | 4/2004 | Fenton |
| 6,733,531 B1 | 5/2004 | Trieu |
| 6,764,514 B1 | 7/2004 | Li |
| 6,770,078 B2 | 8/2004 | Bonutti |
| 6,780,198 B1 | 8/2004 | Gregoire |
| 6,786,989 B2 | 9/2004 | Torriani |
| 6,796,003 B1 | 9/2004 | Marvel |
| 6,818,010 B2 | 11/2004 | Eichhorn |
| 6,823,871 B2 | 11/2004 | Schmieding |
| 6,830,589 B2 | 12/2004 | Erickson |
| 6,860,885 B2 | 3/2005 | Bonutti |
| 6,878,167 B2 | 4/2005 | Ferree |
| 6,890,334 B2 | 5/2005 | Brace |
| 6,893,434 B2 | 5/2005 | Fenton |
| 6,899,722 B2 | 5/2005 | Bonutti |
| 6,913,666 B1 | 7/2005 | Aesclimann |
| 6,916,321 B2 | 7/2005 | TenHuisen |
| 6,921,264 B2 | 7/2005 | Mayer |
| 6,923,824 B2 | 8/2005 | Morgan |
| 6,932,835 B2 | 8/2005 | Bonutti |
| 6,942,684 B2 | 9/2005 | Bonutti |
| 6,944,111 B2 | 9/2005 | Nakamura |
| 6,955,540 B2 | 10/2005 | Mayer |
| 6,955,683 B2 | 10/2005 | Bonutti |
| 6,958,077 B2 | 10/2005 | Suddaby |
| 6,981,983 B1 | 1/2006 | Rosenblatt |
| 6,997,940 B2 | 2/2006 | Bonutti |
| 7,001,411 B1 | 2/2006 | Dean |
| 7,004,959 B2 | 2/2006 | Bonutti |
| 7,008,226 B2 | 3/2006 | Mayer |
| 7,033,379 B2 | 4/2006 | Peterson |
| 7,048,755 B2 | 5/2006 | Bonutti |
| 7,066,960 B1 | 6/2006 | Dickman |
| 7,087,073 B2 | 8/2006 | Bonutti |
| 7,090,111 B2 | 8/2006 | Egan |
| 7,094,251 B2 | 8/2006 | Bonutti |
| 7,104,996 B2 | 9/2006 | Bonutti |
| 7,128,763 B1 | 10/2006 | Blatt |
| 7,018,380 B2 | 12/2006 | Cole |
| 7,147,652 B2 | 12/2006 | Bonutti |
| 7,160,405 B2 | 1/2007 | Aeschlimann |
| 7,179,259 B1 | 2/2007 | Gibbs |
| 7,192,448 B2 | 3/2007 | Ferree |
| 7,217,279 B2 | 5/2007 | Reese |
| 7,217,290 B2 | 5/2007 | Bonutti |
| 7,235,086 B2 | 6/2007 | Sauer |
| 7,241,297 B2 | 7/2007 | Shaolian |
| 7,250,051 B2 | 7/2007 | Francischelli |
| 7,252,685 B2 | 8/2007 | Bindseil |
| 7,273,497 B2 | 9/2007 | Ferree |
| 7,326,200 B2 | 2/2008 | Trieu |
| 7,329,263 B2 | 2/2008 | Bonutti |
| 7,335,205 B2 | 2/2008 | Aeschlimann |
| 7,429,266 B2 | 9/2008 | Bonutti |
| 7,445,634 B2 | 11/2008 | Trieu |
| 7,481,825 B2 | 1/2009 | Bonutti |

(56) References Cited

U.S. PATENT DOCUMENTS

| | | | |
|---|---|---|---|
| 7,481,831 B2 | 1/2009 | Bonutti | |
| 7,488,347 B1 | 2/2009 | Goble | |
| 7,510,895 B2 | 3/2009 | Rateman | |
| 7,556,640 B2 | 7/2009 | Foerster | |
| 7,597,705 B2 | 10/2009 | Forsberg | |
| 7,601,165 B2* | 10/2009 | Stone | A61B 17/0482 606/232 |
| 7,641,694 B1 | 1/2010 | Goble | |
| 7,749,236 B2 | 7/2010 | Oberlaender | |
| 7,854,750 B2 | 12/2010 | Bonutti | |
| 7,879,072 B2 | 2/2011 | BOnutti | |
| 7,891,691 B2 | 2/2011 | Bearey | |
| 7,967,820 B2 | 6/2011 | Bonutti | |
| 8,118,836 B2 | 2/2012 | Denham et al. | |
| 8,128,669 B2 | 3/2012 | Bonutti | |
| 8,140,982 B2 | 3/2012 | Hamilton | |
| 8,147,514 B2 | 4/2012 | Bonutti | |
| 8,162,977 B2 | 4/2012 | Bonutti | |
| 8,298,247 B2* | 10/2012 | Sterrett | A61B 17/0469 606/103 |
| 8,398,680 B2 | 3/2013 | Sauer | |
| 8,425,555 B2 | 4/2013 | Page | |
| 8,771,314 B2 | 7/2014 | Crombie | |
| 8,834,495 B2 | 9/2014 | White | |
| 8,845,699 B2 | 9/2014 | Bonutti | |
| 9,023,058 B2* | 5/2015 | Jaramillo | A61B 17/04 606/103 |
| 9,155,544 B2* | 10/2015 | Bonutti | A61B 17/8852 |
| 9,186,133 B2* | 11/2015 | Gregoire | A61B 17/0401 |
| 9,750,492 B2* | 9/2017 | Ziniti | A61B 17/0487 |
| 9,788,825 B2* | 10/2017 | Whittaker | A61B 17/0401 |
| 10,314,635 B2* | 6/2019 | Gephart | A61B 17/8869 |
| 11,439,351 B2* | 9/2022 | Bremer | A61B 5/6833 |
| 2001/0002440 A1 | 5/2001 | Bonutti | |
| 2001/0008971 A1 | 7/2001 | Schwartz | |
| 2001/0009250 A1 | 7/2001 | Herman | |
| 2001/0041916 A1 | 11/2001 | Bonutti | |
| 2001/0056287 A1 | 12/2001 | Bonutti | |
| 2002/0016593 A1 | 2/2002 | Hearn | |
| 2002/0016633 A1 | 2/2002 | Lin | |
| 2002/0019649 A1 | 2/2002 | Sikora | |
| 2002/0026244 A1 | 2/2002 | Trieu | |
| 2002/0029067 A1 | 3/2002 | Bonutti | |
| 2002/0029083 A1 | 3/2002 | Zucherman | |
| 2002/0029084 A1 | 3/2002 | Paul | |
| 2002/0045902 A1 | 4/2002 | Bonutti | |
| 2002/0058966 A1 | 5/2002 | Tormala | |
| 2002/0062153 A1 | 5/2002 | Paul | |
| 2002/0087189 A1 | 7/2002 | Bonutti | |
| 2002/0103495 A1 | 8/2002 | Cole | |
| 2002/0120269 A1 | 8/2002 | Lange | |
| 2002/0123750 A1 | 9/2002 | Eisermann | |
| 2002/0161439 A1 | 10/2002 | Strobel | |
| 2002/0183762 A1 | 12/2002 | Anderson | |
| 2002/0188301 A1 | 12/2002 | Dallara | |
| 2003/0028196 A1 | 2/2003 | Bonutti | |
| 2003/0039196 A1 | 2/2003 | Nakamura | |
| 2003/0040758 A1 | 2/2003 | Wang | |
| 2003/0065361 A1 | 4/2003 | Dreyfuss | |
| 2003/0083667 A1 | 5/2003 | Ralph | |
| 2003/0097148 A1 | 5/2003 | Valimaa | |
| 2003/0105474 A1 | 6/2003 | Bonutti | |
| 2003/0125749 A1 | 7/2003 | Yuan | |
| 2003/0158555 A1 | 8/2003 | Sanders | |
| 2003/0158582 A1 | 8/2003 | Bonutti | |
| 2003/0118518 A1 | 9/2003 | Hahn | |
| 2003/0167062 A1 | 9/2003 | Gambale | |
| 2003/0167072 A1 | 9/2003 | Oberlander | |
| 2003/0181800 A1 | 9/2003 | Bonutti | |
| 2003/0195514 A1 | 10/2003 | Trieu | |
| 2003/0195530 A1 | 10/2003 | Thill | |
| 2003/0195565 A1 | 10/2003 | Bonutti | |
| 2003/0204204 A1 | 10/2003 | Bonutti | |
| 2003/0204205 A1 | 10/2003 | Sauer | |
| 2003/0208203 A1 | 11/2003 | Lim | |
| 2003/0216742 A1 | 11/2003 | Wetzler | |
| 2003/0225438 A1 | 12/2003 | Bonutti | |
| 2003/0229361 A1 | 12/2003 | Jackson | |
| 2004/0010287 A1 | 1/2004 | Bonutti | |
| 2004/0024459 A1 | 2/2004 | Ferree | |
| 2004/0033034 A1 | 2/2004 | Aeschlimann | |
| 2004/0034357 A1 | 2/2004 | Beane | |
| 2004/0039392 A1 | 2/2004 | Trieu | |
| 2004/0049207 A1 | 3/2004 | Goldfarb | |
| 2004/0097939 A1 | 5/2004 | Bonutti | |
| 2004/0098050 A1 | 5/2004 | Foerster | |
| 2004/0102788 A1 | 5/2004 | Huebner | |
| 2004/0116963 A1 | 6/2004 | Lattouf | |
| 2004/0138703 A1 | 7/2004 | Alleyne | |
| 2004/0138705 A1 | 7/2004 | Heino | |
| 2004/0143334 A1 | 7/2004 | Ferree | |
| 2004/0167548 A1 | 8/2004 | Bonutti | |
| 2004/0172063 A1 | 9/2004 | Li | |
| 2004/0186471 A1 | 9/2004 | Trieu | |
| 2004/0220616 A1 | 11/2004 | Bonutti | |
| 2004/0225325 A1 | 11/2004 | Bonutti | |
| 2004/0230223 A1 | 11/2004 | Bonutti | |
| 2004/0236374 A1 | 11/2004 | Bonutti | |
| 2004/0267361 A1 | 12/2004 | Donnelly et al. | |
| 2005/0033362 A1 | 2/2005 | Grafton | |
| 2005/0033366 A1 | 2/2005 | Cole | |
| 2005/0038514 A1 | 2/2005 | Helm | |
| 2005/0043733 A1 | 2/2005 | Eisermann | |
| 2005/0043796 A1 | 2/2005 | Grant | |
| 2005/0049617 A1* | 3/2005 | Chatlynne | A61B 17/0401 606/148 |
| 2005/0065409 A1 | 3/2005 | de la Torre | |
| 2005/0070765 A1 | 3/2005 | Abdelgany | |
| 2005/0071012 A1 | 3/2005 | Serhan | |
| 2005/0075644 A1 | 4/2005 | DiPoto | |
| 2005/0090827 A1 | 4/2005 | Gedebou | |
| 2005/0096699 A1 | 5/2005 | Wixey | |
| 2005/0113928 A1 | 5/2005 | Cragg | |
| 2005/0125072 A1 | 6/2005 | Kolb | |
| 2005/0126680 A1 | 6/2005 | Aeschlimann | |
| 2005/0143826 A1 | 6/2005 | Zucherman | |
| 2005/0149024 A1 | 7/2005 | Ferrante | |
| 2005/0149029 A1 | 7/2005 | Bonutti | |
| 2005/0203521 A1 | 9/2005 | Bonutti | |
| 2005/0216059 A1 | 9/2005 | Bonutti | |
| 2005/0216087 A1 | 9/2005 | Zucherman | |
| 2005/0222620 A1 | 10/2005 | Bonutti | |
| 2005/0234460 A1 | 10/2005 | Miller | |
| 2005/0240190 A1 | 10/2005 | Gall | |
| 2005/0240227 A1 | 10/2005 | Bonutti | |
| 2005/0246021 A1 | 11/2005 | Ringeisen | |
| 2005/0256582 A1 | 11/2005 | Ferree | |
| 2005/0261684 A1 | 11/2005 | Shaolian | |
| 2005/0261708 A1* | 11/2005 | Pasricha | A61B 17/0401 606/139 |
| 2005/0267481 A1 | 12/2005 | Carl | |
| 2005/0267534 A1 | 12/2005 | Bonutti | |
| 2005/0283246 A1 | 12/2005 | Cauthen | |
| 2006/0009846 A1 | 1/2006 | Trieu | |
| 2006/0009855 A1 | 1/2006 | Goble | |
| 2006/0015101 A1 | 1/2006 | Warburton | |
| 2006/0015108 A1 | 1/2006 | Bonutti | |
| 2006/0024357 A1 | 2/2006 | Carpenter | |
| 2006/0026244 A1 | 2/2006 | Watson | |
| 2006/0064095 A1 | 3/2006 | Senn | |
| 2006/0089646 A1 | 4/2006 | Bonutti | |
| 2006/0122600 A1 | 6/2006 | Cole | |
| 2006/0122704 A1 | 6/2006 | Vresilovic | |
| 2006/0142799 A1 | 6/2006 | Bonutti | |
| 2006/0155287 A1* | 7/2006 | Montgomery | A61F 2/0811 606/313 |
| 2006/0167495 A1 | 7/2006 | Bonutti | |
| 2006/0189982 A1 | 8/2006 | Lange | |
| 2006/0200199 A1 | 9/2006 | Bonutti | |
| 2006/0212073 A1 | 9/2006 | Bonutti | |
| 2006/0217765 A1 | 9/2006 | Bonutti | |
| 2006/0229623 A1 | 10/2006 | Bonutti | |
| 2006/0235413 A1 | 10/2006 | Denham | |
| 2006/0235470 A1 | 10/2006 | Bonutti | |

(56) References Cited

U.S. PATENT DOCUMENTS

| | | | |
|---|---|---|---|
| 2006/0241695 A1 | 10/2006 | Bonutti | |
| 2006/0264953 A1 | 11/2006 | Falahee | |
| 2006/0265009 A1 | 11/2006 | Bonutti | |
| 2006/0265011 A1 | 11/2006 | Bonutti | |
| 2006/0271060 A1 | 11/2006 | Gordon | |
| 2007/0032825 A1 | 2/2007 | Bonutti | |
| 2007/0088362 A1 | 4/2007 | Bonutti | |
| 2007/0118129 A1 | 5/2007 | Fraser | |
| 2007/0198555 A1 | 8/2007 | Friedman | |
| 2007/0233092 A1 | 10/2007 | Falahee | |
| 2007/0245878 A1* | 10/2007 | Harris | G10D 3/14 84/306 |
| 2007/0265561 A1 | 11/2007 | Yeung | |
| 2007/0270833 A1 | 11/2007 | Bonutti | |
| 2008/0021474 A1 | 1/2008 | Bonutti | |
| 2008/0033460 A1 | 2/2008 | Ziniti et al. | |
| 2008/0039845 A1 | 2/2008 | Bonutti | |
| 2008/0039873 A1 | 2/2008 | Bonutti | |
| 2008/0046090 A1 | 2/2008 | Paul | |
| 2008/0097448 A1 | 4/2008 | Binder | |
| 2008/0108897 A1 | 5/2008 | Bonutti | |
| 2008/0108916 A1 | 5/2008 | Bonutti | |
| 2008/0114399 A1 | 5/2008 | Bonutti | |
| 2008/0132950 A1 | 6/2008 | Lange | |
| 2008/0140116 A1 | 6/2008 | Bonutti | |
| 2008/0140117 A1 | 6/2008 | Bonutti | |
| 2008/0195145 A1 | 8/2008 | Bonutti | |
| 2008/0234729 A1 | 9/2008 | Page | |
| 2008/0269753 A1 | 10/2008 | Cannestra | |
| 2008/0269808 A1 | 10/2008 | Gall | |
| 2008/0275477 A1 | 11/2008 | Sterrett et al. | |
| 2009/0024161 A1 | 1/2009 | Bonutti | |
| 2009/0093684 A1 | 4/2009 | Schorer | |
| 2009/0138014 A1 | 5/2009 | Bonutti | |
| 2009/0194969 A1 | 8/2009 | Bearey | |
| 2009/0287188 A1* | 11/2009 | Golden | A61M 25/0147 604/528 |
| 2009/0326562 A1 | 12/2009 | White et al. | |
| 2010/0211120 A1 | 2/2010 | Bonutti | |
| 2010/0069926 A1* | 3/2010 | Goble | A61F 2/30749 606/148 |
| 2010/0087837 A1* | 4/2010 | Jaramillo | A61B 17/8861 606/144 |
| 2011/0060375 A1 | 3/2011 | Bonutti | |
| 2011/0295253 A1 | 12/2011 | Bonutti | |
| 2012/0165841 A1 | 6/2012 | Bonutti | |
| 2012/0191140 A1 | 7/2012 | Bonutti | |
| 2012/0215233 A1 | 8/2012 | Bonutti | |
| 2017/0231622 A1* | 8/2017 | White | A61B 17/06166 29/433 |

FOREIGN PATENT DOCUMENTS

| | | |
|---|---|---|
| CA | 2698057 | 3/2009 |
| DE | 1903316 | 10/1964 |
| DE | 1903016 | 8/1970 |
| DE | 3517204 | 11/1986 |
| DE | 3722538 | 1/1989 |
| DE | 9002844 U1 | 12/1990 |
| EP | 2696338 | 4/1994 |
| EP | 784454 | 5/1996 |
| EP | 773004 | 5/1997 |
| EP | 1614525 | 1/2006 |
| EP | 1988837 | 8/2007 |
| EP | 2134294 | 12/2009 |
| FR | 2717368 | 3/1994 |
| FR | 2728779 | 1/1995 |
| FR | 2736257 | 7/1995 |
| FR | 2750031 | 6/1996 |
| FR | 2771621 | 11/1997 |
| FR | 2785171 | 10/1998 |
| GB | 2093701 A | 9/1982 |
| GB | 2306110 A | 4/1997 |
| JP | 8140982 | 6/1996 |
| WO | 19912779 | 9/1991 |
| WO | 199323094 | 11/1993 |
| WO | 1994008642 | 4/1994 |
| WO | 1995016398 | 6/1995 |
| WO | 1995031941 | 11/1995 |
| WO | 1996014802 | 5/1996 |
| WO | 1997012779 | 4/1997 |
| WO | 1997049347 | 12/1997 |
| WO | 1998011838 | 3/1998 |
| WO | 1998026720 | 6/1998 |
| WO | 2002053011 | 7/2002 |
| WO | 2007092869 | 8/2007 |
| WO | 2008116203 | 9/2008 |
| WO | 2009029908 | 3/2009 |
| WO | 2009124215 | 10/2009 |
| WO | 2010099222 | 2/2010 |

OTHER PUBLICATIONS

Declaration of David Kaplan, Ph.D. Regarding U.S. Pat. No. 5,980,559, IPR 2013-00603, Sep. 24, 2013.
Petition for Inter Partes Review of U.S. Pat. No. 7,087,073, IPR 2013-00604, Filing Date Sep. 24, 2013.
Declaration of Wayne J. Sebastianelli, MD Regarding U.S. Pat. No. 7,087,073, Sep. 24, 2013, IPR 2013-00604.
Petition for Inter Partes Review of U.S. Pat. No. 6,500,195, IPR 2013-00624, Filing Date Oct. 2, 2013.
Declaration of Dr. Philip Hardy in Support of Petition for Inter Partes Review of U.S. Pat. No. 6,500,195, IPR 2013-00624, Sep. 25, 2013.
Petition for Inter Partes Review of U.S. Pat. No. 5,527,343, IPR 2013-00628, Filing Date Sep. 25, 2013.
Declaration of Dr. Philip Hardy in Support of Petition for Inter Partes Review of U.S. Pat. No. 5,527,343, IPR 2013-00628, Sep. 25, 2013.
Corrected Petition for Inter Partes Review of U.S. Pat. No. 5,921,986, IPR 2013-00631, Filing Date Sep. 27, 2013.
Expert Declaration of Steve E. Jordan, MD, for Inter Partes Review of U.S. Pat. No. 5,921,986, IPR 2013-00631, Sep. 24, 2013.
Corrected Petition for Inter Partes Review of U.S. Pat. No. 8,147,514, IPR 2013-00632, Filing Date Sep. 27, 2013.
Declaration of Steve Jordan for U.S. Pat. No. 8,147,514, from IPR 2013-00632, dated Sep. 23, 2013 (exhibit 1009).
Corrected Petition for Inter Partes Review of U.S. Pat. No. 8,147,514, IPR 2013-00633, Filing Date Sep. 27, 2013.
Declaration of Steve Jordan for U.S. Pat. No. 8,147,514, from IPR 2013-00633, dated Sep. 23, 2013 (exhibit 1006).
Flory, Principles of Polymer Chemistry, 1953, selected pages (cited in IPR 2013-00603, exhibit 1012).
Grizzi, Hydrolytic degradation of devices based on poly(DL-lactic acid) size-dependence, Biomaterials, 1995, vol. 16, No. 4, p. 305-11 (cited in IPR 2013-00603, exhibit 1006).
Gopferich, Mechanisms of polymer degradation and erosion, Biomaterials, 1996, vol. 17, No. 2, p. 103-114 (cited in IPR 2013-00603, exhibit 1013).
Gao et el, Swelling of Hydroxypropyl Methylcellulose Matrix Tablets . . . , Journal of Pharmaceutical Sciences, vol. 85, No. 7, Jul. 1996, p. 732-740 (cited in IPR 2013-00603, exhibit 1014).
Linvatec, Impact Suture Anchor brochure, 2004 (cited in IPR 2013-00628, exhibit 1010).
Seitz et al, Repair of the Tibiofibular Syndesmosis with a Flexible Implant, J_ of Orthopaedic Trauma, vol. 5, No. 1, p. 78-82, 1991 (cited in IPR 2013-00631, exhibit 1007) (cited in 2013-00632).
Translation of FR2696338 with translator's certificate dated Sep. 17, 2013 (cited in IPR 2013-00631, 2013-00632).
Translation of DE9002844.9 with translator's certificate dated Sep. 26, 2013 (cited in IPR 2013-00631, 2013-00632).
Declaration of Steve Jordan for U.S. Pat. No. 5,921,986, from IPR 2013-00632, dated Sep. 24, 2013 (exhibit 1010).
Declaration of Steve Jordan for U.S. Pat. No. 5,921,986, from IPR 2013-00633, dated Sep. 24, 2013 (exhibit 1007).
Declaration of Dr. Steve E. Jordan for U.S. Pat. No. 8,147,514, from IPR 2013-00631, dated Sep. 23, 2013.

(56) References Cited

OTHER PUBLICATIONS

The Search for the Holy Grail: A Centrury of Anterior Cruciate Ligament Reconstruction, R. John Naranja, American Journal of Orthopedics, Nov. 1997.
Femoral Bone Plug Recession in Endoscope Anterior Cruciate Ligament Reconstruction, David E. Taylor, Arthroscopy: The Journal of Arthroscopic and Related Surgery, Aug. 1996.
Meniscus Replacement with Bone Anchors: A Surgical Technique, Arthroscopy: The Journal of Arthroscopic and Related Surgery, 1994.
Problem Solving Report Question No. 1014984.066, Ultrasonic Welding, (c) 1999.
Branson, Polymers: Characteristics and Compatibility for Ultrasonic Assembly, Applied Technologies Group, Publication unknown.
Enabling Local Drug Delivery-Implant Device Combination Therapies, Surmodics, Inc., (c) 2003.
Stent Based Delivery of Sirolimus Reduces Neointimal Formation in a Porcine Coronary Model, Takeshi Suzuki, American Heart Association, Inc. (c) 2001.
Why Tie a Knot When You Can Use Y-Knot?, Innovasive Devices Inc., (c) 1998.
Ask Oxford, compact Oxford English dictionary: projection, Mar. 30, 2009.
Ask Oxford, compact Oxford English dictionary: slit, Mar. 30, 2009.
Textured Surface Technology, Branson Technolog, Branson Ultrasonics Copr., (c) 1992.
Arthrex, Protect your graft, Am J Sports Med, vol. 22, No. 4, Jul.-Aug. 1994.
Barrett et al, T-Fix endoscopic meniscal repair: technique and approach to different types of tears, Apr. 1995, Arthroscopy vol. 11 No. 2 p. 245-51.
Cope, Suture Anchor for Visceral Drainage, AJR, vol. 148 p. 160-162, Jan. 1986.
Gabriel, Arthroscopic Fixation Devices, Wiley Enc. of Biomed Eng., 2006.
Innovasive, We've got you covered, Am J Sports Med, vol. 26, No. 1, Jan.-Feb. 1998.
510k—TranSet Fracture Fixation System, Feb. 24, 2004, k033717.
510k—Linvatec Biomaterials modification of Duet and impact Suture Anchor, Nov. 19, 2004, k042966.
510k, arthrex pushlock, Jun. 29, 2005, K051219.
510k, mitek micro anchor, Nov. 6, 1996, K962511.
510k, Multitak Suture System, Jan. 10, 1997, K964324.
510k, Modified Mitek 3.5mm Absorbable Suture Anchor System, Jun. 9, 1997, K970896.
510k, Summary for Arthrex Inc. 's Bio-Interference Screw, Jul. 9, 1997, K971358.
510k, Surgicraft Bone Tie, Sep. 25, 1998, K982719.
Karlsson et al, Repair of Bankart lesions with a suture anchor in recurrent dislocation of the shoulder, Scand. j. of Med & Science in Sports, 1995, 5:170-174.
Madjar et al, Minimally Invasive Pervaginam Procedures, for the Treatment of Female Stress Incontinence . . . , Artificial Organs, 22 (10) 879-885, 1998.
Nowak et al, Comparative Study of Fixation Techniques in the Open Bankart Operation Using Either a Cannulated Screw or Suture-Anchors, Acta Orthopcedica Belgica, vol. 64—2—1998.
Packer et al, Repair of Acute Scapho-Lunate Dissociation Facilitated by the "Tag"* Suture Anchor, Journal of Hand Surgery (British and European Volume, 1994) 198: 5: 563-564.
Richmond, Modificatio of the Bankart reconstruction with a suture anchor, Am J Sports Med, vol. 19, No. 4, p. 343-346, 1991.
Shea et al, Technical Note: Arthroscopic Rotator Cuff Repair Using a Transhumeral Approach to Fixation, Arthroscopy: The Journal of Arthroscopic and Related Surgery, vol. 14, No. 1 (Jan.-Feb.), 1998: pp. 118-122.
Tfix, Acufex just tied the knot . . . , Am. J. Sports Med., vol. 22, No. 3, May-Jun. 1994.
Wong et al, Case Report: Proper Insertion Angle Is Essential to Prevent Intra-Articular Protrusion of a Knotless Suture Anchor in Shoulder Rotator Cuff Repair, Arthroscopy: The Journal of Arthroscopic and Related Surgery, vol. 26, No. 2 Feb. 2010: pp. 286-290.
Cobb et al, Late Correction of Malunited Intercondylar Humeral Fractures Intra-Articular Osteotomy and Tricortical Bone Grafting, J BoneJointSurg [Br] 1994; 76-B:622-6.
Fellinger, et al, Radial avulsion of the triangular fibrocartilage complex in acute wrist trauma: a new technique for arthroscopic repair, Jun. 1997, Arthroscopy vol. 13 No. 3 p. 370-4.
Hecker et al , Pull-out strength of suture anchors for rotator cuff and Bankart lesion repairs, Nov.-Dec. 1993 , The American Journal of Sports Medicine, vol. 21 No. 6 p. 874-9.
Hernigou et al , Proximal Tibial Osteotomy for Osteoarthritis with Varus Deformity a Ten to Thirteen-Year Follow-up Study, J Bone Joint Surg, vol. 69-A, N0.3. Mar. 1987, p. 332-354.
Ibarra et al, Glenoid Replacement in Total Shoulder Arthroplasty, the Orthopedic Clinics of Northamerica: Total Shoulder Arthroplasty, vol. 29 No. 3, Jul. 1998 p. 403-413.
Mosca et al, Calcaneal Lengthening for Valgus Deformity of the Hindfoot: Results in Children Who Had Severe, Symptomatic fLATFOOT and Skewfoot, J Bone Joint Surg,, 1195—p. 499-512.
Murphy et al , Radial Opening Wedge Osteotomy in Madelung's Deformity, J. Hand Surg, vol. 21 A No. 6 Nov. 1996, p. 1035-44.
Biomet, Stanmore Modular Hip, J. Bone Joint Surg., vol. 76-B : No. Two, Mar. 1994.

\* cited by examiner

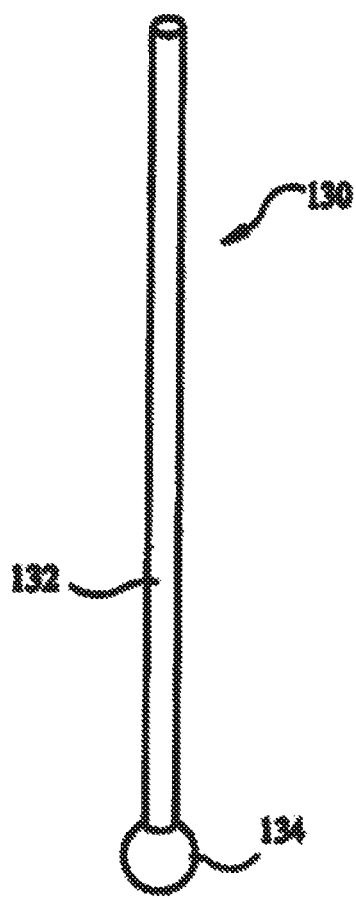 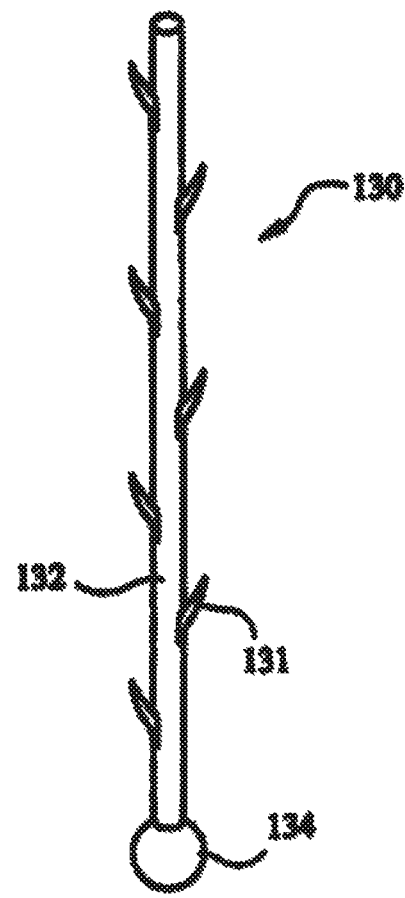
FIG. 9A    FIG. 9B
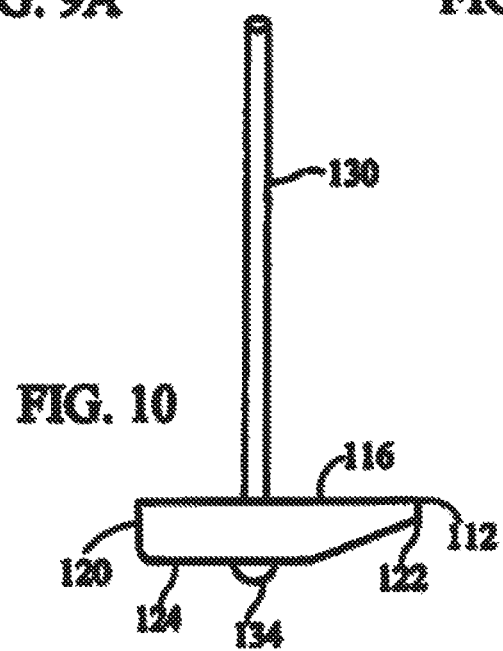
FIG. 10

TISSUE FIXATION SYSTEM AND METHOD

CROSS-REFERENCE TO RELATED APPLICATION

This Application claims priority to U.S. Provisional Patent Application No. 60/889,605, entitled Tissue Fixation System and Method, filed on Feb. 13, 2007, the contents of which are incorporated herein by reference in their entirety.

FIELD OF THE INVENTION

The invention relates to a system and method for fixation and stabilization of tissue. In particular, the invention relates to minimally invasive bone fracture fixation and stabilization.

BACKGROUND OF THE INVENTION

It is well-known in the medical arts that applying pressure to tissue helps during the healing process. Incised or torn soft tissue, for example, may be approximated with bandages, sutures, or staples. Proper and more rapid healing of broken or fractured bones likewise may be facilitated by applying constant pressure to the bone. For instance, physicians may insert pins, screws, or bolts in the area of the fracture in order to apply pressure to the fracture.

However, inserting screws through or around fractures can be complex and time-consuming. For example, the process of inserting a screw typically involves multiple steps conducted from multiple incisions or openings that provide access to the treated bone or tissue, including the steps of drilling holes, measuring the relevant distances to determine the appropriate screw selection, tapping the hole to establish threads, and screwing the screw into the hole.

In addition to the length and complexity of the process, bone screws also may lose their grip and strip out of the bone. In addition, currently available lag screws also typically provide only one side of cortex fixation and are generally not suited for percutaneous surgery. Moreover, when placing the screws in the bone, the physician may not accurately set the screw into the distal hole or may miss the distal hole completely, thereby resulting in the screw stripping the threads or breaking the bone.

Many devices and instruments have been disclosed to fasten soft and hard tissue for enhanced healing or tissue reconstruction. Examples of such devices include bone plates, bone wraps, external bone supports, and the like.

For example, U.S. Pat. No. 5,921,986, the contents of which are incorporated herein by reference, discloses a bone suture and associated methods for implantation and fracture fixation. The '986 Patent describes fasteners and anchors used in conjunction with an elongate fixation element, such as a suture. In some cases, it may be advantageous to use more rigid fixation elements.

Accordingly, a need exists for a tissue fixation instrument which can provide flexible or rigid fixation of tissue while accessing the tissue from a small skin portal.

SUMMARY OF THE INVENTION

The present invention relates to a tissue fixation system. The system comprises an elongate fastening member and a fastener moveable with respect to the elongate fastening member from a first orientation to a second orientation, the fastener having a body with a tissue contacting surface that includes a groove configured and dimensioned to receive a portion of the elongate member in the first orientation. The system can also include a second fastener or other means for maintaining tension in the elongate fastening member.

A biasing means can be provided to maintain the fastener in the first orientation. The biasing means can be an adhesive between the groove and the portion of the elongate fastening member received in the groove. The biasing means could also be a frangible connection between the groove and the portion of the elongate fastening member received in the groove.

The fastener body can have a free surface opposite the tissue contacting surface, with the free surface including a channel configured and dimensioned to receive a portion of the elongate member in the first orientation. The fastener body can also include a through bore extending from the tissue contacting surface through the free surface.

In one embodiment, the fastener body includes leading and trailing ends. The leading end can be tapered or otherwise shaped to facilitate insertion. The groove terminates at the through bore and extends toward one of the leading and trailing ends and the channel terminates at the through bore and extends toward the other of the leading and trailing ends. In an exemplary embodiment, the groove extends toward the leading end and the channel extends toward the trailing end.

The free surface of the fastener body can be provided with a well surrounding the through bore. The well can be configured and dimensioned to receive at least a portion of the stop. A distal end of the elongate fastening member can include a stop larger than the through bore.

The present invention also relates to a medical instrument or device for securing the fastener with respect to the elongate fastening member. The medical device tensions the elongate fastening member and crimps either the fastener or a bushing. Another aspect of the invention relates to methods of tissue fixation using the disclosed tissue fixation systems.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 9A shows an elongate fastening member according to the present invention;

FIG. 9B shows an elongate fastening member including expandable members;

FIG. 10 shows a fastener in a second orientation with respect to an elongate fastening member;

DETAILED DESCRIPTION OF THE INVENTION

The present invention provides a tissue fixation system for dynamic and rigid fixation of tissue. The system can be utilized for the fixation and stabilization of body tissue, including soft tissue to soft tissue, soft tissue to bone, and bone to bone. The surgical system can additionally be used to affix implants and grafts to body tissue. The system can access and treat fractured, incised or torn tissue, or the like, from one access area (i.e., from only one opening to the tissue to be fastened) instead of requiring two or more openings. That is, the system is a linear fixation system that can be used with a single, small incision or portal in the skin or other soft tissue to gain access to the fractured bone. The fixation system may be an all-in-one system, packaged as a system kit, for creating a passage in tissue, positioning fasteners, and tensioning an elongate fastening member, like a suture, thread, cable, wire, rod, or pin. The individual components of the system can either be reusable or single use components.

Figure 1:
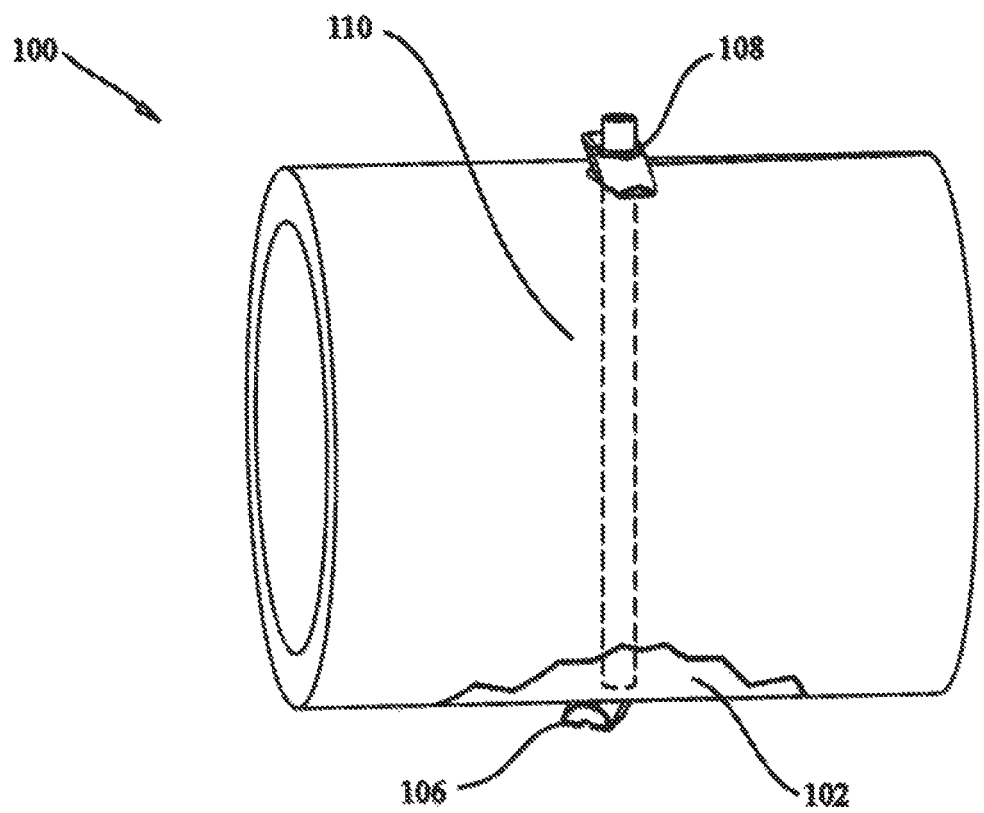
FIG. 1 shows a schematic illustration of a tissue fixation system according to the present invention utilized for fracture fixation.
Figure 2:
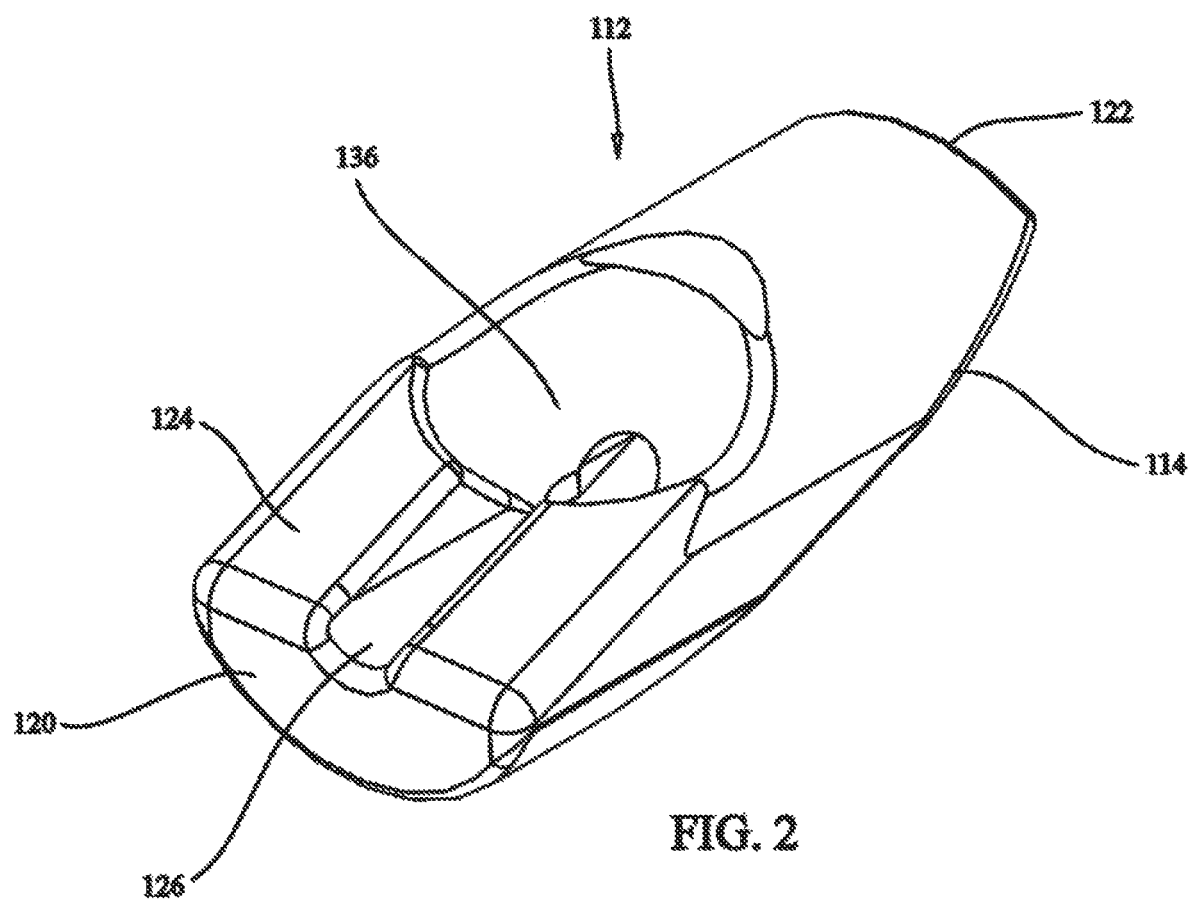
FIG. 2 shows a perspective view of a fastener according to the present invention.
Figure 3:
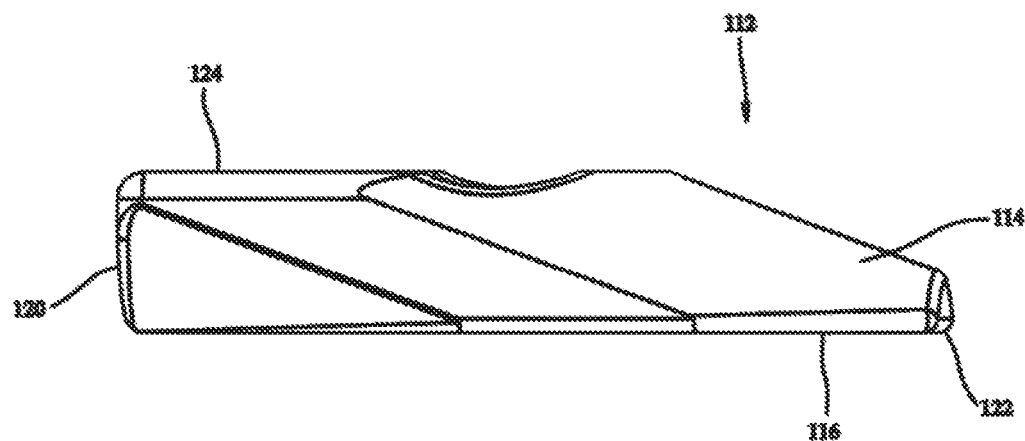
FIG. 3 shows a side view of the fastener of FIG. 2.
Figure 4:
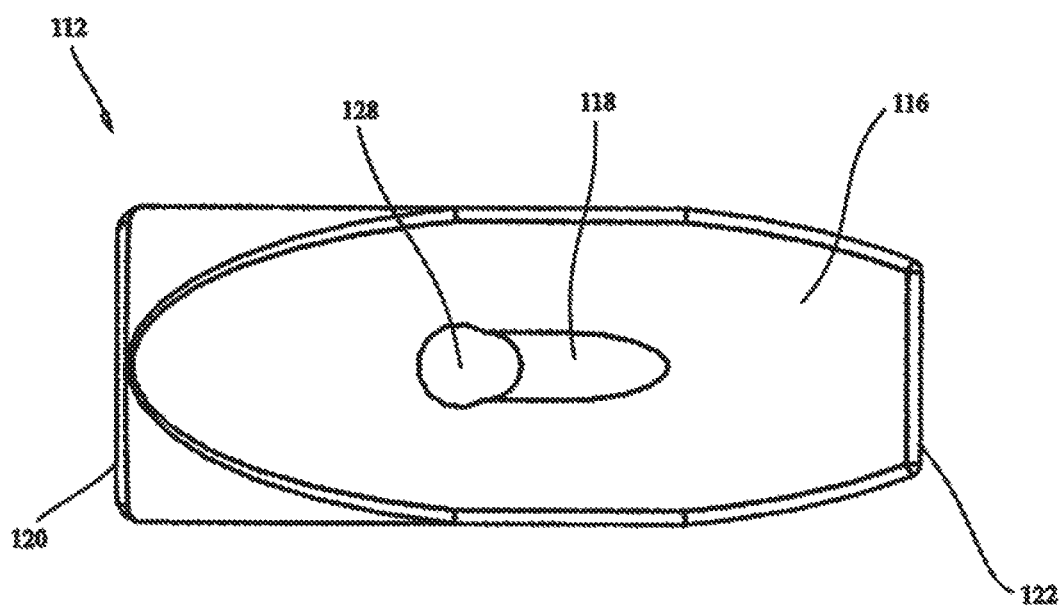
FIG. 4 shows a bottom view of the fastener of FIG. 2.

Referring now to the drawing figures in which like reference designators refer to like elements, FIG. 1 shows an exemplary embodiment of a tissue fixation system 100 according to the present invention. A fractured portion 102 of a bone 104 is approximated by system 100. Use of system 100 is not limited to any particular type of fracture. Furthermore, use of system 100 is not limited to fracture fixation. In other words, system 100 can be utilized for other tissue fixation applications (such as soft tissue) or similar clinical indications. Examples of such tissue includes, are not limited to, muscle, cartilage, ligament, tendon, skin, etc. Also, the tissue may be stomach tissue, and the system may be used during bariatric surgery, as in stomach stapling. Additionally, the system 100 can be used for the fixation of implants to tissue.

In this regard, the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include breast implants, biodegradable plates, porcine or bovine patches, metallic fasteners, compliant bearing for medial compartment of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

Although the invention is described primarily on a macroscopic level, it is also envisioned that the present invention can be used for microscopic applications. For example, in the repair of nerve tissue, individual cells or fibers may need to be repaired. Similarly, muscle repair may require tightening of individual muscle fibers.

System 100 includes a distal fastener 106 contacting fracture portion 102, a proximal fastener 108 contacting bone 104, and an elongate fastening member 110 extending through the fracture and coupling distal and proximal fasteners 106, 108. Tension is maintained in elongate fastening member 110 to press fasteners 106, 108 against opposite sides of bone 104 with a desired force. This force presses fracture portion 102 against bone 104 firmly together to promote healing of the fracture. If desired, buttons or other force distributing members could be provided between fasteners 106, 108 and the bone. Although FIG. 1 shows distal and proximal fasteners 106, 108 as having the same construction, they could have differing construction. However, for convenience and practical purposes, it may be beneficial if distal and proximal fasteners 106 and 108 have substantially the same construction.

Figure 5:
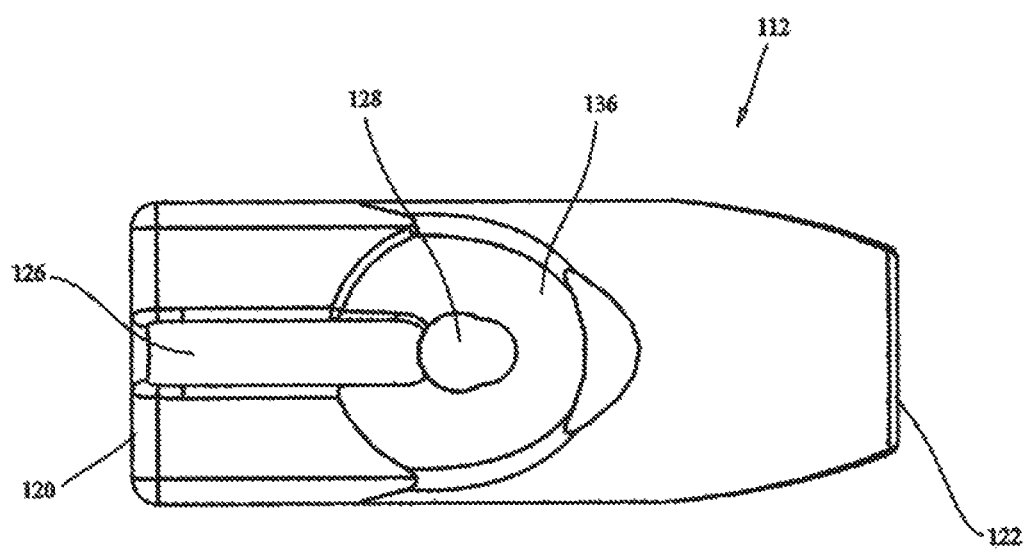
FIG. 5 shows a top view of the fastener of FIG. 2.
Figure 6:
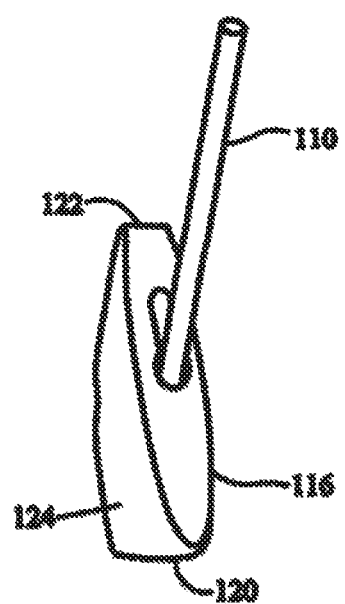
FIG. 6 shows a fastener and elongate fastening member with the fastener in a first orientation with respect to the elongate fastening member.

FIGS. 2-5 show an exemplary embodiment of a fastener 112 that can be used as part of system 100, i.e. as either or both of distal and proximal fasteners 106, 108. Fastener 112 has a body 114 that is configured and dimensioned to facilitate implantation through minimally invasive procedures, e.g. through a cannula or sleeve. In particular, body 114 includes a tissue contacting surface 116 that is provided with groove 118 that receives a portion of elongate fastening member 110 when fastener 112 is in a first orientation with respect to elongate fastening member 110. This is seen in FIG. 6. The accommodation of elongate fastening member 110 within groove 118 helps to minimize the profile of the assembly of fastener 112 and elongate fastening member 110. The reduced profile can be more readily passed through a cannula or sleeve. If desired, an adhesive can be provided within groove 118 to bias fastener 112 in the first orientation. Alternatively, a frangible connection can be provided between groove 118 and a portion of elongate fastening member 110, operative to keep fastener 112 in the first orientation with respect to elongate fastening member 110, until the frangible connection is broken, when desired.

Figure 7:
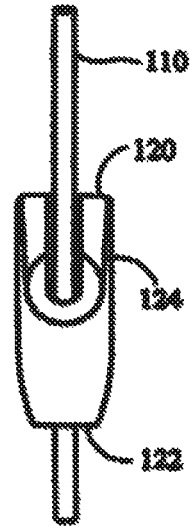
FIG. 7 shows a front view of a fastener in the first orientation with respect to the elongate fastening member with the fastener rotated 180° compared to FIG. 6.
Figure 8:
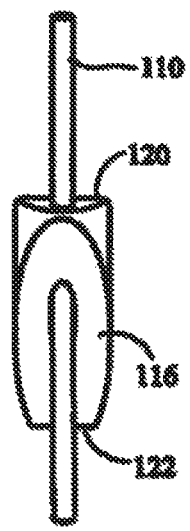
FIG. 8 shows a back view of the fastener and elongate fastening member of FIG. 7.

Fastener 112 is provided with first and second ends 120, 122. As shown in FIG. 6, first end 120 is the leading end and second end 122 is the trailing end. In this position, when fastener 112 is pivoted to a second orientation, like distal fastener 106 of FIG. 1, tissue contacting surface 116 is in contact with the tissue. As shown in FIGS. 7 and 8, second end 122 is the leading end and first end 120 is the trailing end. In this position, when fastener 112 is pivoted to the second orientation, like proximal fastener 108 of FIG. 1, tissue contacting surface 116 is in contact with the tissue.

Fastener body 114 has a free surface 124 opposite tissue contacting surface 116. Free surface 124 is provided with a channel 126 that receives a portion of elongate fastening member 110 when fastener 112 is in a first orientation with respect to elongate fastening member 110. As shown in FIGS. 7 and 8, fastener 112 is being slid along elongate fastening member 110. In particular, a through bore 128 extends from tissue contacting surface 116 through free surface 124. Through bore 128 is larger in diameter than elongate fastening member 110 so that fastener 112 freely slides along elongate fastening member 110. A portion of elongate fastening member 110 fits within channel 126 on free surface 124 and a portion of elongate fastening member 110 fits within groove 118 on tissue contacting surface 116.

Fastener body 114 is shown with first end 120 having a substantially flat profile and second end 122 having a tapered profile. In general, any suitable external configuration can be used for fastener 112. Examples of fasteners may be found in U.S. Pat. Nos. 5,163,960; 5,403,348; 5,464,426; 5,549,630; 5,593,425; 5,713,921; 5,718,717; 5,782,862; 5,814,072; 5,814,073; 5,845,645; 5,921,986; 5,948,002; 6,010,525; 6,045,551; 6,159,234; 6,368,343; 6,447,516; 6,475,230; 6,592,609; 6,635,073; and 6,719,765. Other fastener types are disclosed in U.S. patent application Ser. Nos. 10/102,413; 10/228,855; 10/779,978; 10/780,444; 10/797, 685, and 11/358,331. The above cited patents and patent applications are hereby incorporated by reference.

Fastener 112 can be made of any biocompatible material suitable for a given application. For example, the fasteners may be, but are not limited to, degradable, biodegradable, bioerodible, bioabsorbable, mechanically expandable, hydrophilic, bendable, deformable, malleable, riveting, threaded, toggling, barbed, bubbled, laminated, coated, blocking, pneumatic, one-piece, multi-component, solid, hollow, polygon-shaped, pointed, self-introducing, and combinations thereof. Also, the fasteners may include metallic material, polymeric material, ceramic material, composite material, body tissue, synthetic tissue, hydrophilic material, expandable material, compressible material, heat bondable material, and combinations thereof. Examples of body tissue include bone, collagen, cartilage, ligaments, or tissue graft material like xenograft, allograft, and autograft. The fasteners may also be made from a porous matrix or mesh of biocompatible and bioresorbable fibers acting as a scaffold to regenerate tissue.

The fasteners may further be made of or have a coating made of an expandable material. The material could be compressed then allowed to expand. Alternatively, the material could be hydrophilic and expand when it comes in contact with liquid. Examples of such expandable materials are ePTFE and desiccated body tissue.

Moreover, the fasteners described herein and incorporated by reference may include therapeutic substances to promote healing. These substances could include antibiotics, hydroxyapatite, anti-inflammatory agents, steroids, antibiotics, analgesic agents, chemotherapeutic agents, bone morphogenetic protein (BMP), demineralized bone matrix, collagen, growth factors, autogenetic bone marrow, progenitor cells, calcium sulfate, immo suppressants, fibrin, osteoinductive materials, apatite compositions, germicides, fetal cells, stem cells, enzymes, proteins, hormones, cell therapy substances, gene therapy substances, and combinations thereof. These therapeutic substances may be combined with the materials used to make the fasteners to produce a composite fastener. Alternatively, the therapeutic substances may be impregnated or coated on the fastener. Time-released therapeutic substances and drugs may also be incorporated into or coated on the surface of the fastener. The therapeutic substances may also be placed in a bioabsorbable, degradable, or biodegradable polymer layer or layers.

FIG. 9A shows an exemplary embodiment of an elongate fastening member 130. Elongate fastening member 130 includes a body 132 and has a stop 134 at a distal end. Body 132 can be selected for a given application. For example, if a rigid elongate fastening member 130 is needed, body 132 can be a rod or a tube. If a more flexible elongate fastening member 130 is needed, body 132 can be a suture. In general, a wire analogous to those used for cerclage of bone fractures is believed to provide a suitable combination of strength and flexibility. Although body 132 is shown as a single strand wire, the invention can be used with any type of surgical cable, such as a multi-strand cable.

Stop 134 can be made integral with body 132 or separate and then attached. Stop 134 is larger in diameter than through bore 128 in body 114 of fastener 112. Thus, once stop 134 reaches through bore 128, fastener 112 cannot be slid any further along elongate fastening member 130. As shown in FIG. 5, free surface 124 of fastener 112 is provided with a well 136 surrounding through bore 128. Well 136 is configured and dimensioned to receive at least a portion of stop 134. As shown in FIG. 10, this helps reduce the profile of the assembly when fastener 112 is in a second orientation with respect to elongate fastening member 130.

Referring to FIG. 9B, in another embodiment, the elongated fastener member 130 includes expandable members 131, positioned along the body 132. Upon insertion into the tissue, the expandable members 131 expand to engage the surrounding tissue. For examples, the expandable members 131 can be barbs. The barbs 131 engage the surrounding tissue, maintaining elongated fastener member's 130 position within the tissue.

The elongate fastening members of the present invention may be made of metallic material, non-metallic material, composite material, ceramic material, polymeric material, co polymeric material, or combinations thereof. The members may be degradable, biodegradable, bioabsorbable, or nonbiodegradable. Examples of suture materials that can be used for the elongate fastening members are polyethylene, polyester, cat gut, silk, nylon, polypropylene, linen, cotton, and copolymers of glycolic and lactic acid. Preferably, the members are flexible or bendable. They may be threadlike, monofilament, multifilament, braided, or interlaced. The members may have a coating of therapeutic substances or drugs. For example, the members may include antibiotics, hydroxyapatite, anti-inflammatory agents, steroids, antibiotics, analgesic agents, chemotherapeutic agents, bone morphogenetic protein, demineralized bone matrix, collagen, growth factors, autogenetic bone marrow, progenitor cells, calcium sulfate, immo suppressants, fibrin, osteoinductive materials, apatite compositions, fetal cells, stem cells, enzymes, proteins, hormones, and germicides.

Figure 11:
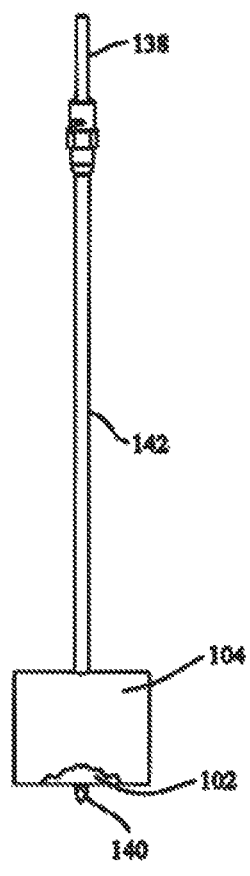
FIG. 11 shows a cannulated drill system used to create a passage through the tissue to be fixed.

The use of the tissue fixation system according to the present invention will now be described using fracture fixation as an example. If necessary, the fracture is reduced bringing fracture portion 102 into contact with bone 104 (FIG. 11). The reduction can be achieved using any number of techniques.

Figure 12:
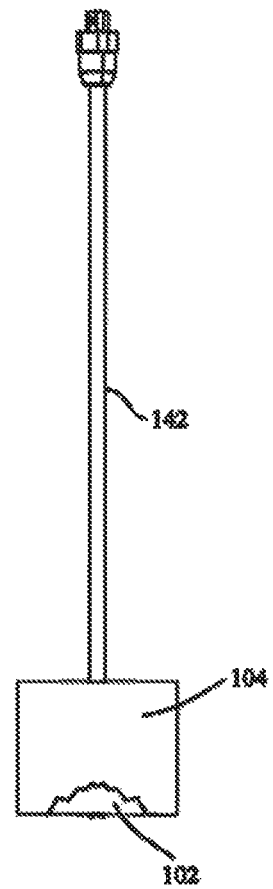
FIG. 12 shows a sleeve having a lumen through which the fixation system can be passed.

As also shown in FIG. 11, a drill system 138 is used to drill across the fracture, thereby creating a passage completely through bone 104. Drill system 138 includes a drill bit 140 with a headpiece configured for attachment to a drill. A drill stop can be placed on the headpiece and prevents drill bit 140 from penetrating too far beyond the tissue to be drilled. Drill system 138 may be a cannulated drill system that fits over a k-wire or other similar guide wire. A cannula or sleeve 142 may encircle drill bit 140 or at least the shaft portion of drill bit 140. As drill bit 140 creates a passage through bone 104, sleeve 142 is positioned in the passage. Drill system 138 is used to create a passage in bone 104 from the proximal side of bone 104 to the distal side of bone 104, then the drill and drill bit 140 are removed from sleeve 142 (FIG. 12).

Figure 13:
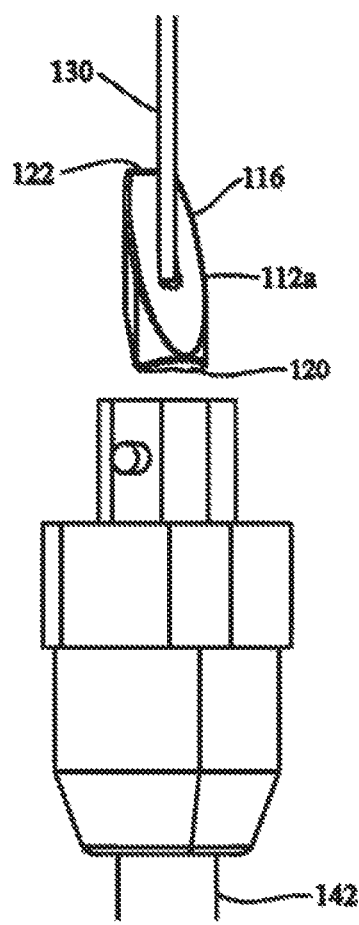
FIG. 13 shows a distal fastener being inserted into the sleeve.
Figure 14:
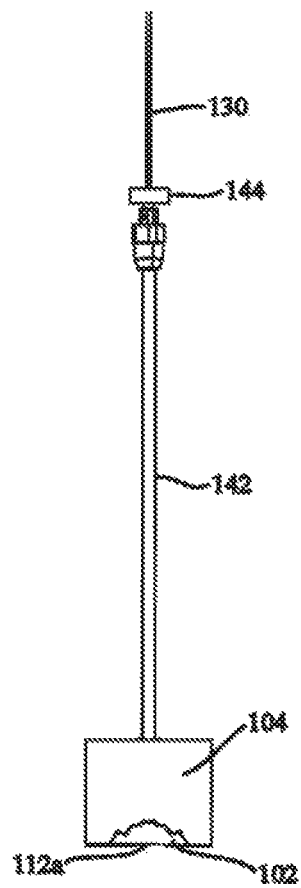
FIG. 14 shows a pushrod used to move the distal fastener through the sleeve.
Figure 15:
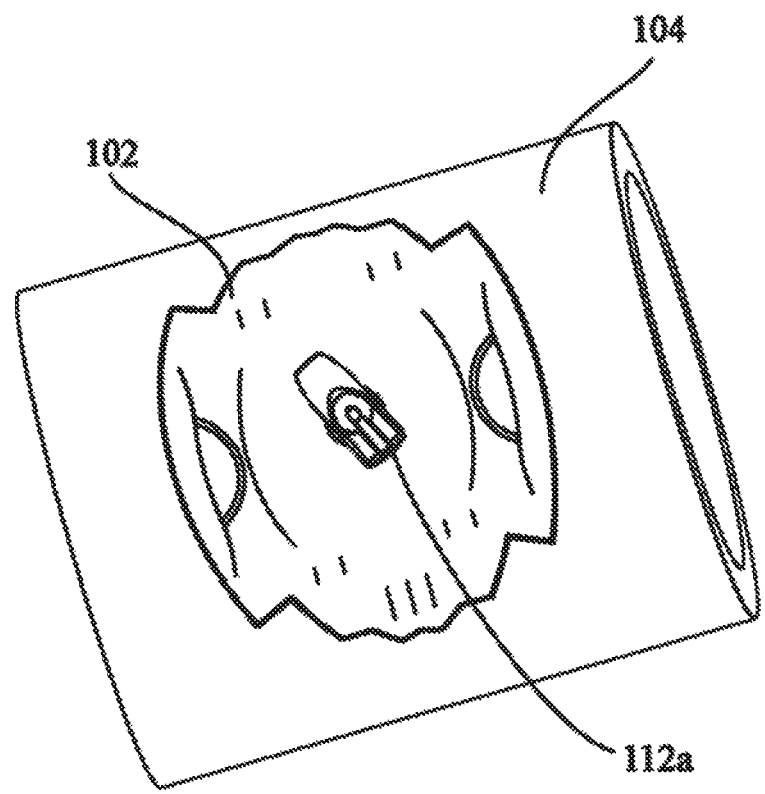
FIG. 15 shows the distal fastener in the second orientation.

As shown in FIG. 13, a distal fastener 112a is inserted into sleeve 142. Distal fastener 112a is inserted in the first orientation with respect to elongate fastening member 130 with first end 120 as the leading end. In this configuration, tissue contacting surface 116 will be in contact with fracture portion 102 when distal fastener 112a is pivoted into the second orientation. This is best seen in FIGS. 14 and 15, in which a pushrod 144 is used to advance distal fastener 112a and elongate fastening member 130 through sleeve 142. Pushrod 144 also facilitates the pivoting of distal fastener 112a from the first orientation to the second orientation. This pivoting is not possible until distal fastener 112a has exited through sleeve 142. Also, because the length of distal fastener 112a is larger than the passage created in bone 104, pulling back on elongate fastening member 130 helps to ensure distal fastener 112a is in the second orientation and flush against fracture portion 102.

Figure 16:
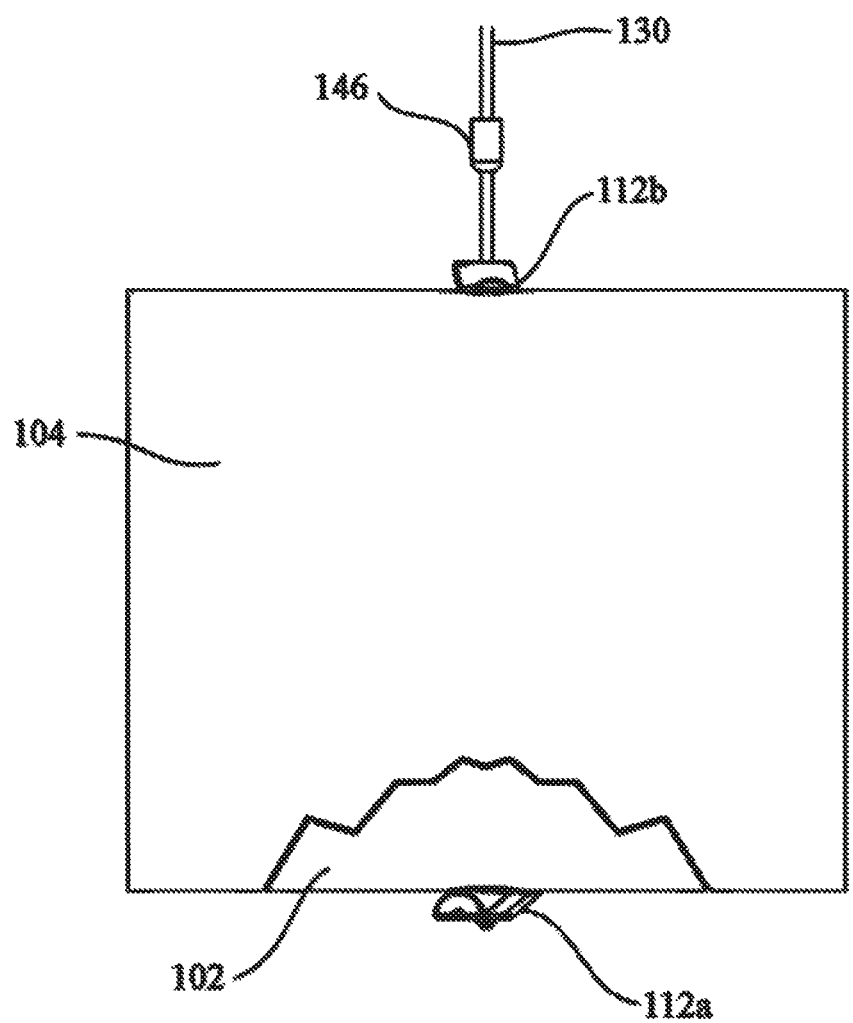
FIG. 16 shows a proximal fastener being used to maintain the tension in the elongate fastening member.

As illustrated in FIG. 16, sleeve 142 is removed from bone 104. Fastener 112a is located on the distal side of bone 104. Elongate fastening member 130 extends from fastener 112a through the bone passage and out the proximal opening of the bone or tissue passage. Any suitable means can be used to keep distal fastener 112a against fracture portion 102 with tension, where the tension can be measure and controlled in accordance with use. For example, elongate fastening member 130 can be deformed at the proximal end of the passage such that the deformed section rests against bone 104. The deformation would depend on the nature of elongate fastening member 130. If elongate fastening member 130 is a relatively flexible element, such as a suture, cable, or wire, then simply tying a knot in fastening member 130 could be sufficient to maintain the tension. If elongate fastening member 130 does not allow a knot, such as would be the case with a rod or tube, then mechanical deformation of elongate fastening member 130 to create an enlarged head could be sufficient to maintain the tension. U.S. Patent Application Publication No. US 2002/0016593, the contents of which are incorporated herein by reference, discloses mechanisms to mechanically deform an extension member and could be used to deform elongate fastening member 130.

Alternatively, the elongated fastening member 130 can be deformed by an energy source, such as thermal energy, to deform elongate fastening member 130 to create an enlarged head sufficient to maintain the tension.

In an exemplary embodiment, a proximal fastener 112b is used to secure distal fastener 112a and elongate fastening member 130. In this embodiment, proximal fastener 112b is identical to distal fastener 112a. If not already pre-loaded, proximal fastener 112b is loaded onto elongate fastening member 130. Proximal fastener 112b is loaded as shown in FIGS. 7 and 8, i.e. with second end 122 as the leading end so that after proximal fastener 112b is slid down against bone 104 and pivoted into the second orientation, tissue contacting surface 116 is in contact with bone 104.

Elongate fastening member 130 is tensioned, and proximal fastener 112b is secured to elongate fastening member 130 to thereby approximate the fracture and stabilize bone 104. The tension of elongate fastening member 130 pulls on distal and proximal fasteners 112a, 112b generally toward each other, thereby applying pressure to the fractured bone or tissue. In this regard, a bushing 146 can be used to secure proximal fastener 112b with the desired tension. Single or multiple elongated members 130 can be used to secure the fractured bone or tissue.

Although a number of mechanisms can be used to secure bushing 146, an instrument or medical device particularly useful for this will now be described.

In this regard, the present invention also provides a medical device for securing a fastener against relative movement with respect to a cable. As previously disclosed, a cable and pair of oppositely spaced fasteners can be used to secure a bone fracture. The cable is passed through the bone and fracture; a first fastener secures the cable on a first side (fracture side) of the bone; and a second fastener is positioned about the cable on a second side of the bone, opposite the first fastener. A bushing is positioned onto the cable to secure the second fastener against the second side of the bone. A force is applied to the bushing, compressing the second fastener against the second side of the bone and providing a tension to the cable. The tension in the cable can be measured and controlled, for example, with the use of a sensor and spring element. The spring can apply the force to tension the cable, and the sensor can be used to measure the resulting tension. Alternatively, the sensor can measure the compression of the tissue to determine the tension. The bushing is crimped about the cable, securing the second fastener against the second side of the bone, such that a tension is provided through the cable between the first and second fasteners.

Figure 17:
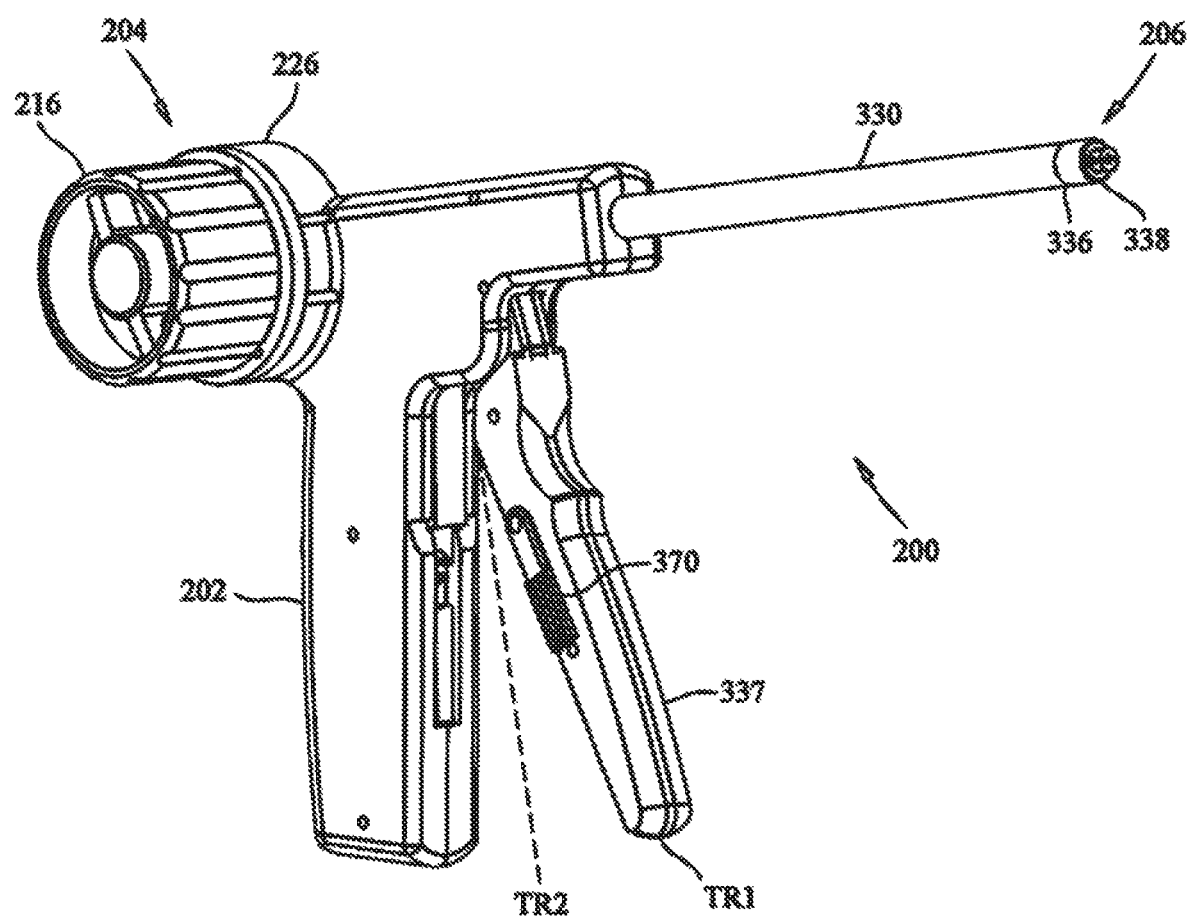
FIG. 17 depicts a front isometric view of a medical device in accordance with the present invention.

Referring now to FIG. 17, a medical device 200 in accordance with an embodiment of the invention is provided for securing the bushing to the cable. Medical device 200 includes handle portion 202 having a tensioning mechanism 204, operative to tension cable 110/132 and apply a force to bushing 146, and a crimping mechanism 206 operative to securing bushing 146 to cable 110 or 132 of system 100 or member 130.

Figure 18:
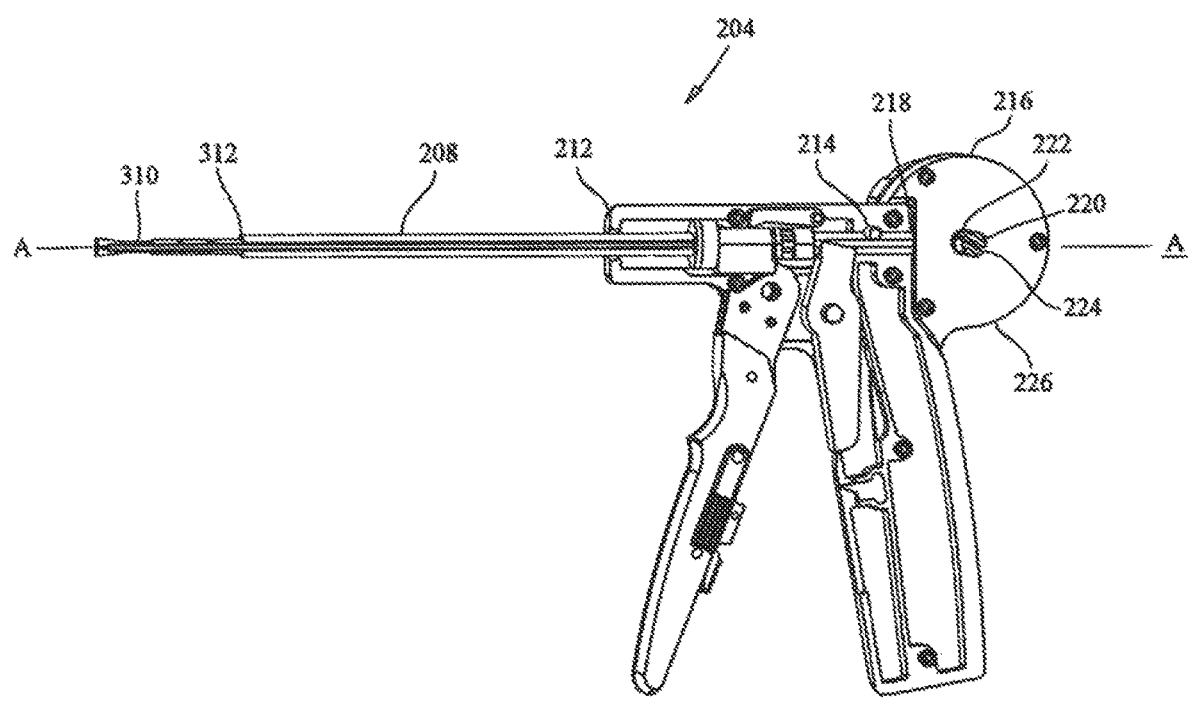
FIG. 18 depicts a sectional view showing the tensioning mechanism of the medical device of FIG. 17.

With additional reference to FIG. 18, tensioning mechanism 204 includes collet holder 208 defining a longitudinal passage along a central longitudinal axis A-A. Collet holder 208 is fixedly positioned through top portion 212 of handle portion 202, secured by collet holder pin 214. A cable tensioner 216 is positioned proximal to a first end 218 of the collet holder 208. Cable tensioner 216 includes rotatable shaft 220 aligned with the longitudinal passage of the collet holder 208. Rotatable shaft 220 includes a cable aperture 222 (visible in FIGS. 20,21) for threading the cable therethrough, wherein cable 132 is wrapped about rotatable shaft 220 to thereby prevent relative movement between cable 132 and cable tensioner 216.

Figure 19:
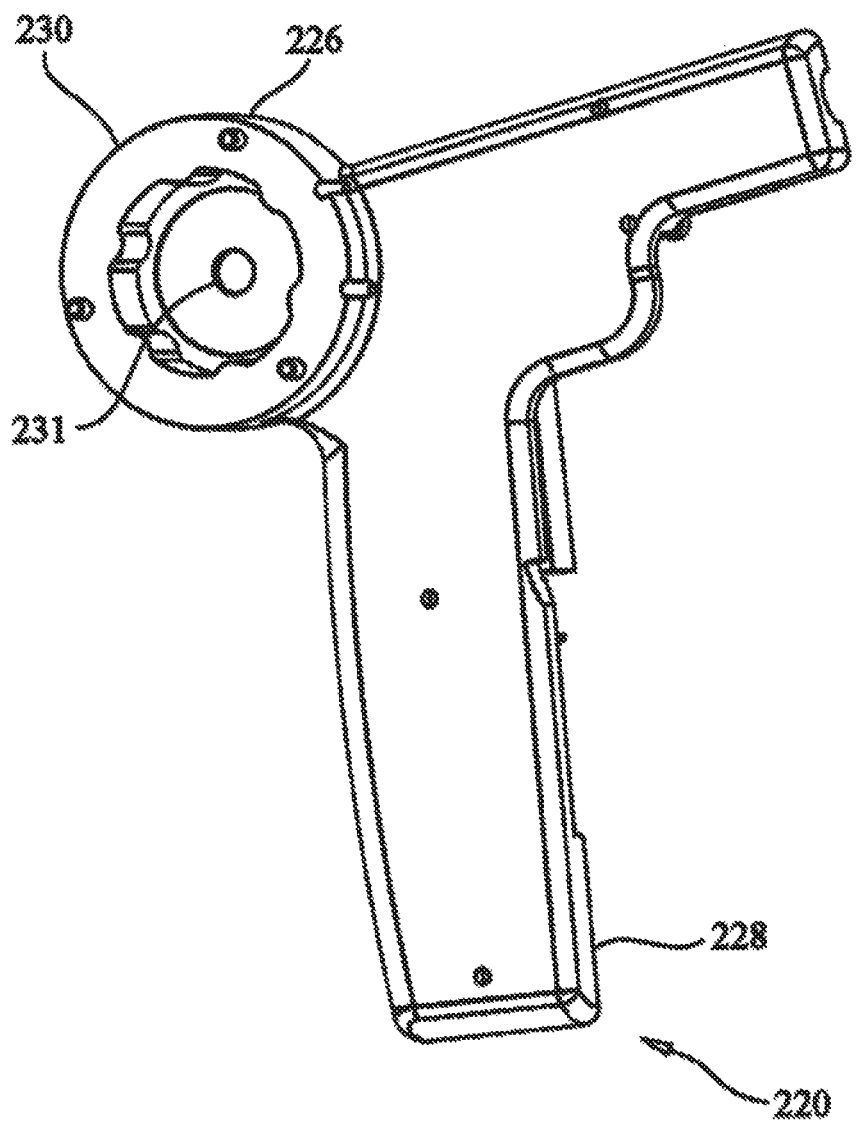
FIG. 19 depicts a side isometric view showing the tensioner housing of the medical device of FIG. 17.

Referring to FIG. 19, tensioner housing 226 is affixed to first portion 228 of handle portion 202. Tensioner housing 226 includes recess 230, configured for receiving tensioning assembly 232 of cable tensioner 216, wherein rotatable shaft 220 extends through center hole 231 in tensioner housing 226.

Figure 20:
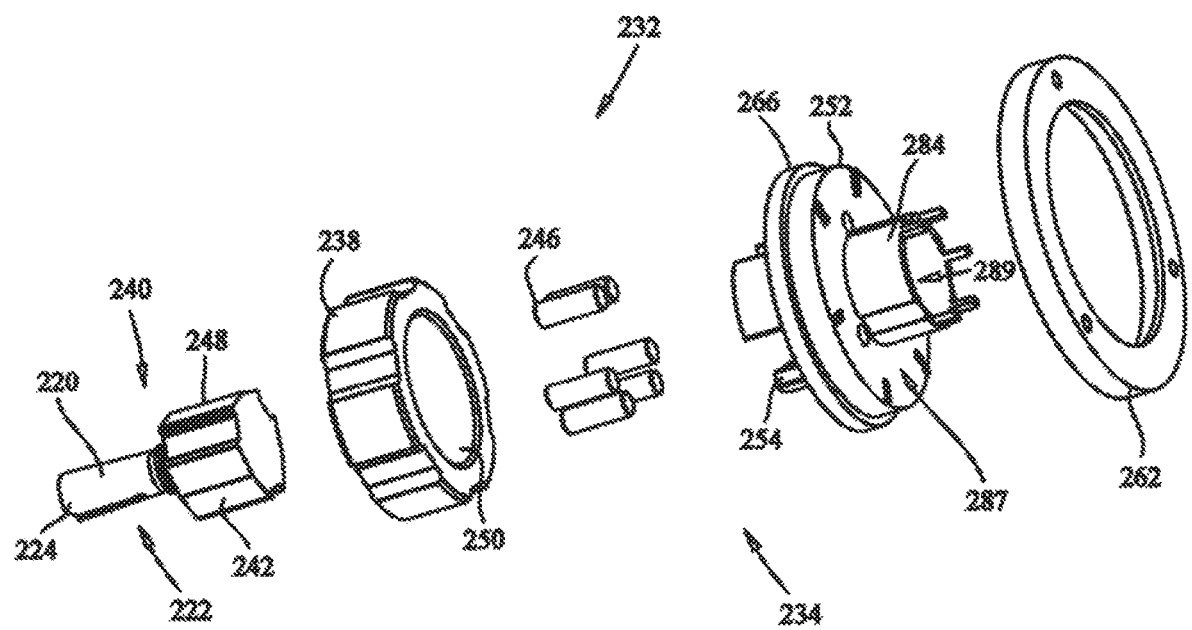
FIG. 20 depicts an exploded view of the locking assembly of the medical device of FIG. 17.
Figure 21:
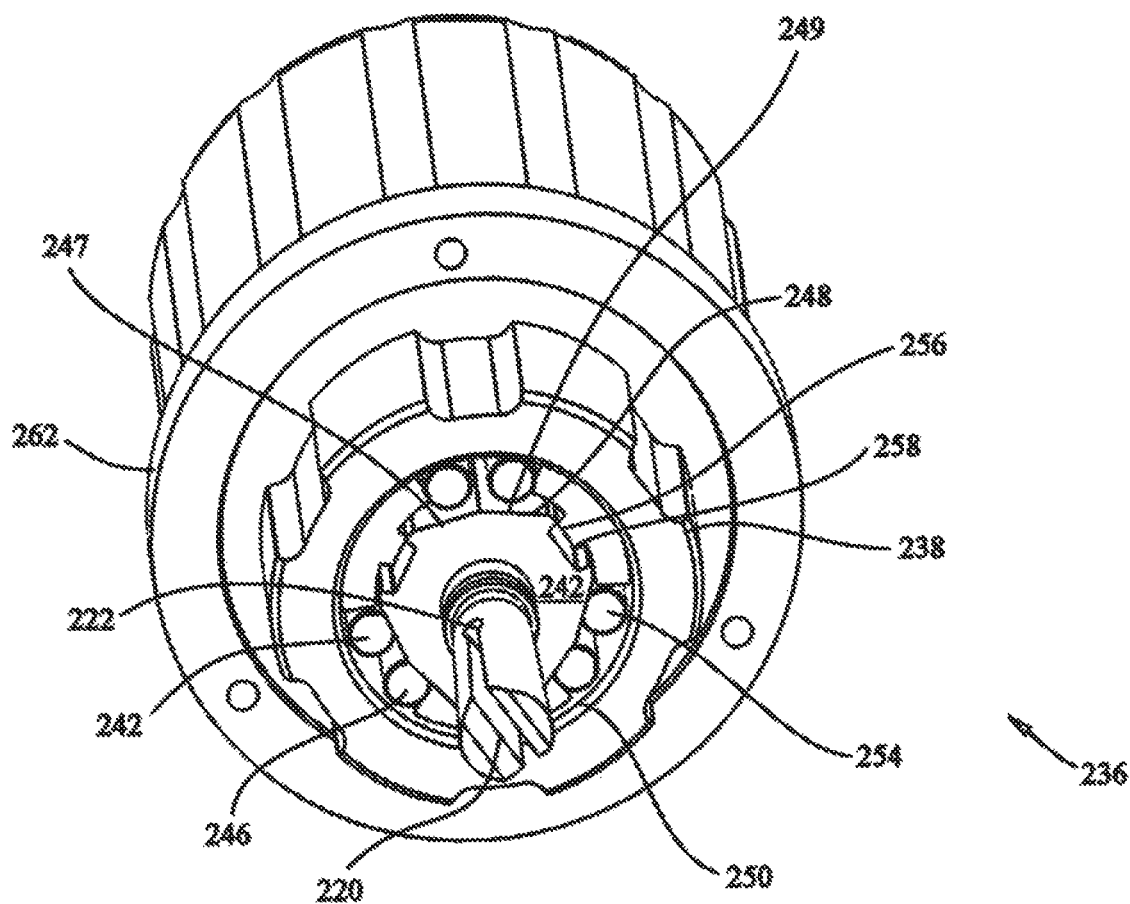
FIG. 21 depicts a rear isometric view of the locking assembly of the medical device of FIG. 17.

Referring to FIGS. 20 and 21, tensioning assembly 232 includes locking assembly 234. Locking assembly 234 includes inner housing 238, which is press fit into recess 230 of tensioner housing 226 when assembled. Inner housing 238 is sized and dimensioned to prevent rotation of inner housing 238 with respect to tensioner housing 226. Output shaft 240 is positioned partly within inner housing 238, and includes rotatable shaft 220 and shaft head 242. Output shaft 240 is positioned such that rotatable shaft 220 is extended through center hole 231 in tensioner housing 226, and shaft head 224 is positioned within inner housing 238.

Roller bearings 246 are positioned between an outer raised surface 248 of shaft head 242 and inner surface 250 of the inner housing 238. The roller bearings 246 are fitted between shaft head 242 and inner housing 238, to allow rotation of output shaft 240 with respect to inner housing 238.

Outer raised surface 248 of shaft head 242 is provided in a substantially triangular configuration, having, in the embodiment shown, three sets of pairs of oppositely inclined surfaces, as represented by surfaces 247,249. Roller bearings 246 are positioned, one each, between inclined surfaces 247,249 and inner surface 250 of inner housing 238, such that a rotation of shaft head 250 will pinch or compress roller bearings 246 between inclined surfaces 247,249 and inner surface 250. In this manner, shaft head 242 and output shaft 240 become rotationally locked together, and are mutually prevented from rotating with respect to inner housing 238. As such, no external torsional force is required to produce a locking coupling. In either direction of rotation, clockwise or counter clockwise, at least three roller bearings 246 will be pinched, locking shaft head 242 and output shaft 240 from rotational movement.

Inner extensions 254 of cam plate 252 are positioned between inner surface 250 of inner housing 238 and shaft head 242. Inner extensions 254 include raised portions 256 configured to engage notched sections 258 of shaft head 242, locking the cam plate 252 to output shaft 240, such that rotation of cam plate 252 will rotate output shaft 240. In this manner, cam plate 252 is rotationally coupled to output shaft 240.

Inner extensions 254 are further operative to unlock shaft head 242 and output shaft 240. Specifically, when cam plate 252 is rotated, inner extensions 254 dislodge and prevent pinching of roller bearings 246, thus allowing rotation of shaft head 242 and output shaft 240. When rotation of cam plate 252 in discontinued, roller bearings 246 will again be allowed to be pinched, locking shaft head 242 and output shaft 240.

Cam plate 252 further includes radial flange 260 disposed about an outer circumference. Retaining ring 262 is positioned over cam plate 252, engaging flange 260 and affixed to tensioner housing 226. In this manner, cam plate 252, output shaft 240, roller bearings 246, and inner housing 238 are secured within recess 231 of tensioner housing 226 by retaining ring 262. Engagement of flange 260 and retaining ring 262 secures cam plate 252 in position, yet allows for rotation of cam plate 252 with respect to tensioner housing 226.

Figure 22:
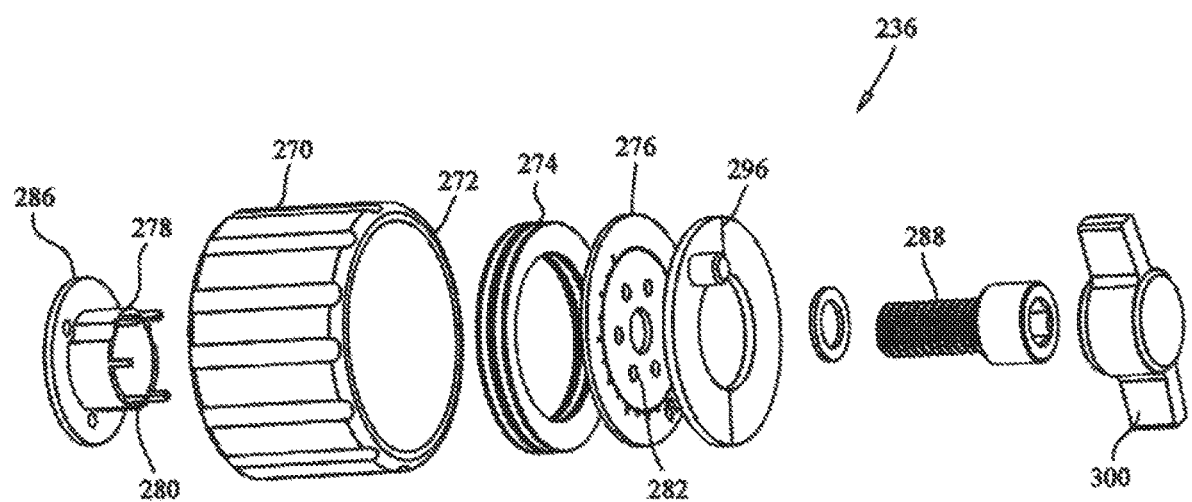
FIG. 22 depicts an exploded view of the rotation assembly of the medical device of FIG. 17.

Referring to FIG. 22, tensioning assembly 232 further includes rotation assembly 236. Rotation assembly 236 includes winding knob 270 defining knob recess 272. Biasing member 274 is positioned in knob recess 272, where compression plate 276 is positioned over biasing member 274. Locking collar 278 is positioned through the bottom of winding knob 270, extending through biasing member 274 such that extensions 280 of locking collar 278 are positioned in alignment holes 282 of compression plate 276.

Figure 23:
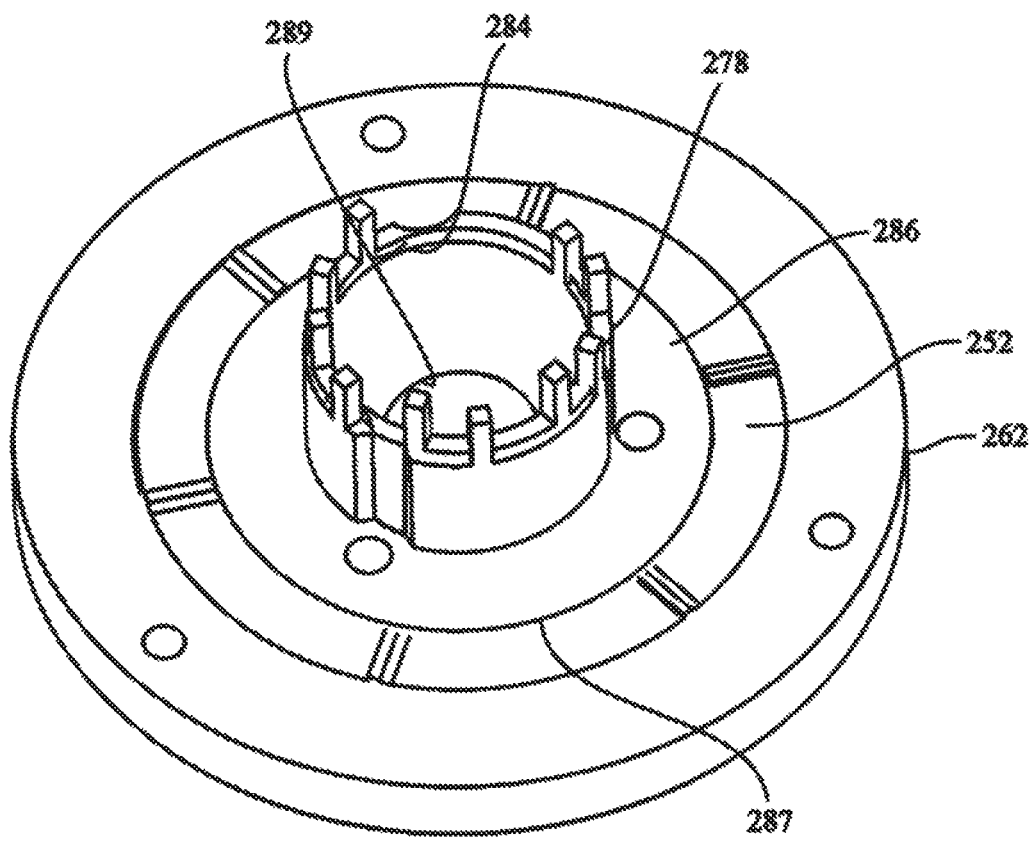
FIG. 23 depicts partial isometric view of the connection of the rotation assembly of FIG. 22 to the locking assembly of FIG. 21.

Referring also to FIG. 23, rotation assembly 236 is affixed to locking assembly 234 by attachment of locking collar 278 to cam plate 252. Locking collar 278 is positioned to overlap upper collar portion 284 of cam plate 252, wherein upper collar portion 284 extends through locking collar 278. Flanged portion 286 of locking collar 278 is affixed to top surface 287 of cam plate 252. Locking collar 278 can be affixed to cam plate 252 with screws, rivets, welding, or other mechanical or chemical means.

The combined locking collar 278 and upper collar portion 284 of cam plate 252 extend through the bottom of winding knob 270, extending through biasing member 274 and engaging alignment holes 282 of compression plate 276. An adjustment bolt 288 is positioned through compression plate 276, threadably engaging threaded hole 289 (not visible) in cam plate 252, securing rotation assembly 236 to locking assembly 234.

Figure 24:
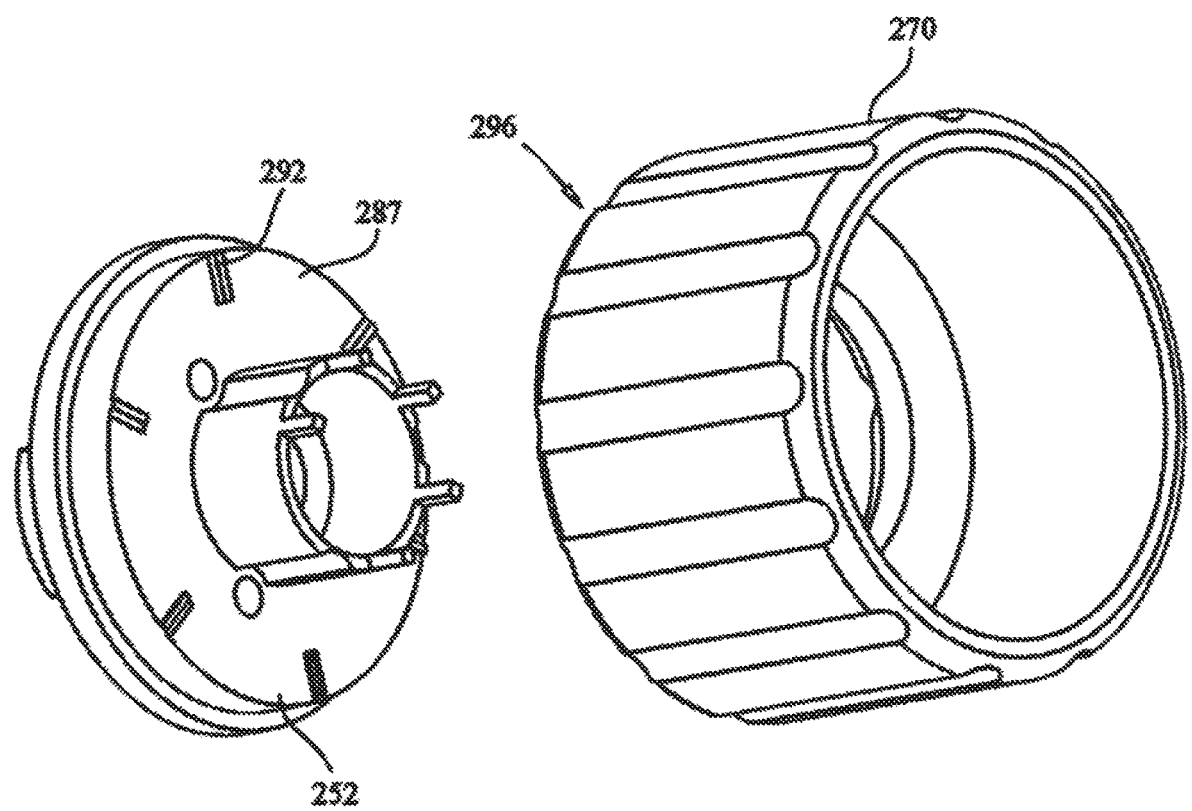
FIG. 24 depicts a partial front exploded view of the torque controller of the tensioning mechanism.
Figure 25:
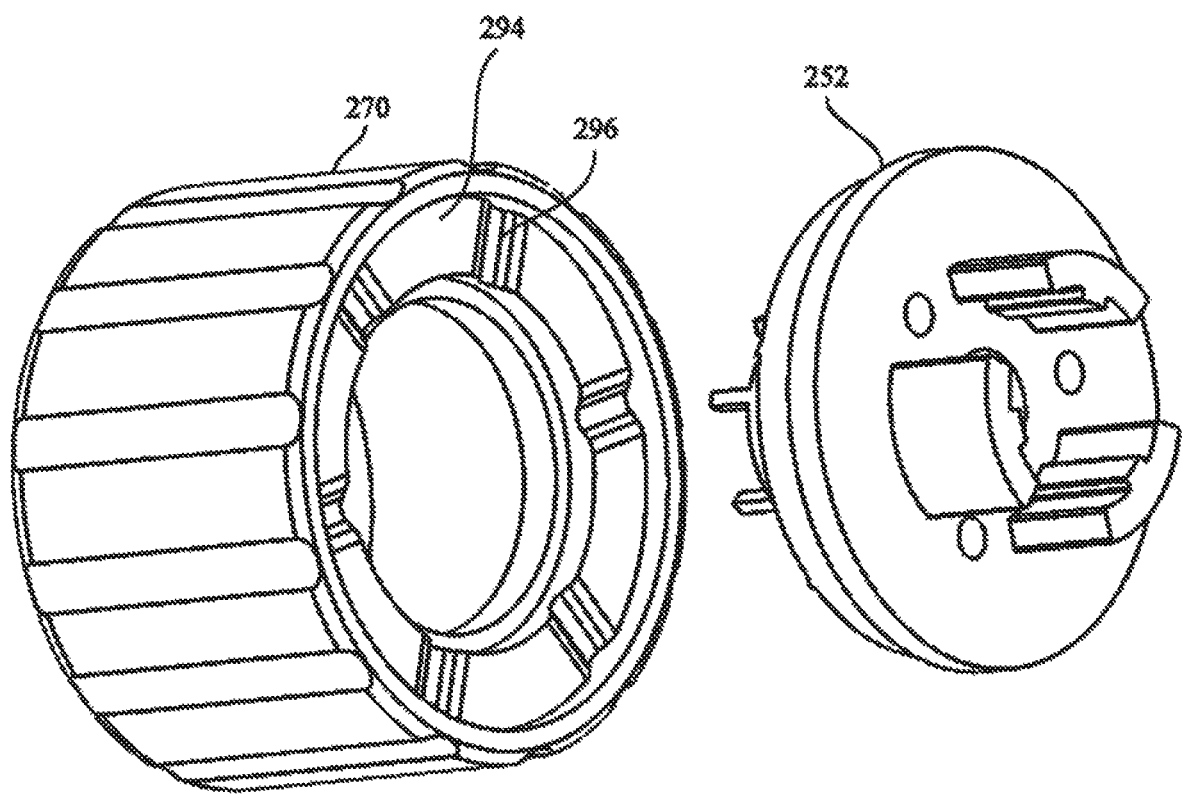
FIG. 25 depicts a partial rear exploded view of the torque controller of the tensioning mechanism.

Connection of rotation assembly 236 to locking assembly 234 includes an automatic torque control. Referring to FIGS. 24 and 25, top surface 287 of cam plate 252 includes a plurality of raised radial sections 292. Bottom surface 294 of winding knob 270 includes a plurality of mating notched sections 296 (not visible), one for each of the raised radial sections 292 of cam plate 252. Raised radial sections 292 and notched section 296 are configured to engage each other, whereby rotation of winding knob 270 will cause engagement of sections 292,296 to cause rotation of cam plate 252.

Winding knob 270 is urged into engagement with cam plate 252 by biasing member 274. Force applied by biasing member 274 can be controlled by rotating adjustment bolt 288. Tightening of adjustment bolt 288 urges compression plate 276 onto biasing member 274, increasing force applied between them. Loosening of adjustment bolt 288 raises compression plate 276 away from biasing member 274, decreasing applied force.

In use, biasing member 274 applies force to winding knob 270, forcing winding knob 270 into engagement with cam plate 252. Applied force is translated to a desired tension in cable 132. Torsional force is applied to winding knob 270 during rotation of winding knob 270, wrapping cable 132 about rotatable shaft 220, increasing tension in cable 132. At tensions less than a desired tension, applied force is sufficient to maintain engagement between winding knob 270 and cam plate 252.

However, at tensions greater then a desired tension, applied force is insufficient to maintain engagement between winding knob 270 and cam plate 252. As such, as an increased torque is applied to winding knob 270, winding knob 270 and cam plate 252 will lose engagement, wherein notched sections 296 of winding knob 270 will skip over raised radial sections 292 of cam plate 252. In this manner, tension greater then a desired tension cannot be applied to cable 132. Furthermore, locking assembly 234 prevents reversing, or backing off of cam plate 252, thus maintaining tension in cable 132.

Figure 26:
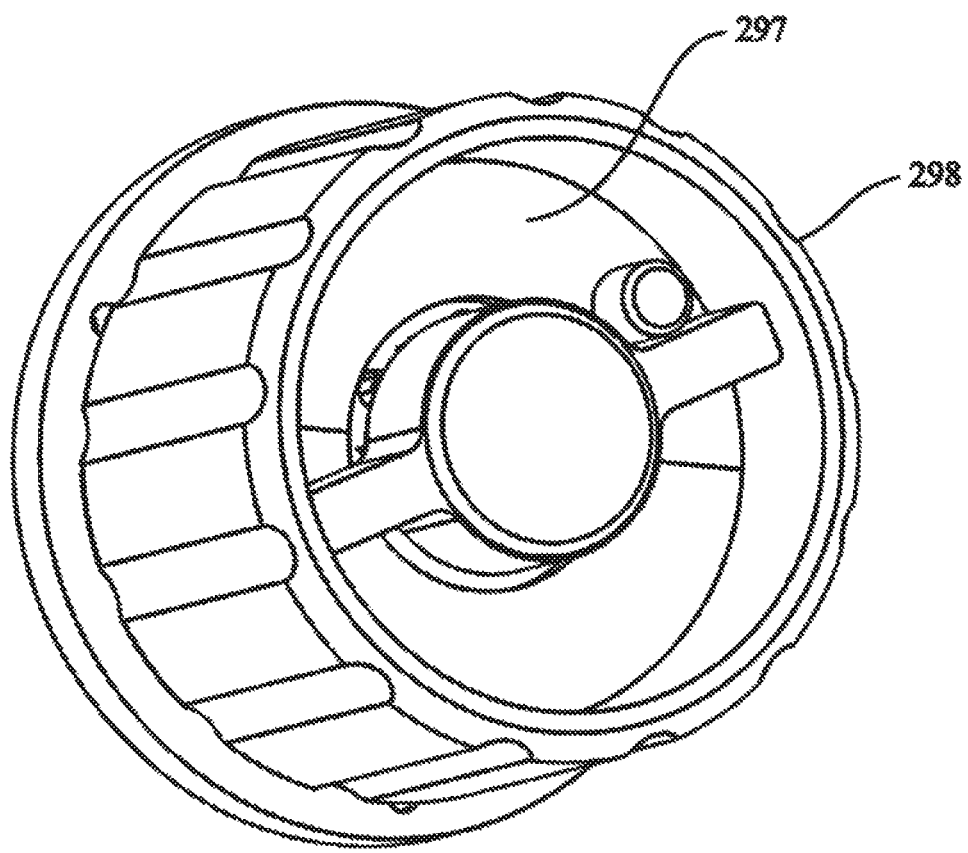
FIG. 26 depicts a partial front isometric view of the rotation assembly of FIG. 22.

Referring to FIG. 26, cover plate 297 can be positioned over and affixed to compression plate 276 cover plate 297 can include limit stop 298, for limiting maximum allowable tension on cable. Thumb cap 300 can be attached to the head of adjustment bolt 288 to facilitate adjustment. Thumb cap 300 is designed to engage limit stop 298, thus preventing an over adjust of adjustment bolt 288.

Cover plate 297 can include tension indicating markings to indicate desired tension to be applied to cable 132. Thumb cap 300 is rotated to a desired tension, as indicated by the markings, enabling a user to select a desired tension based on cable strength, or may be used to prevent over tensioning or snapping of cable 132.

Figure 27:
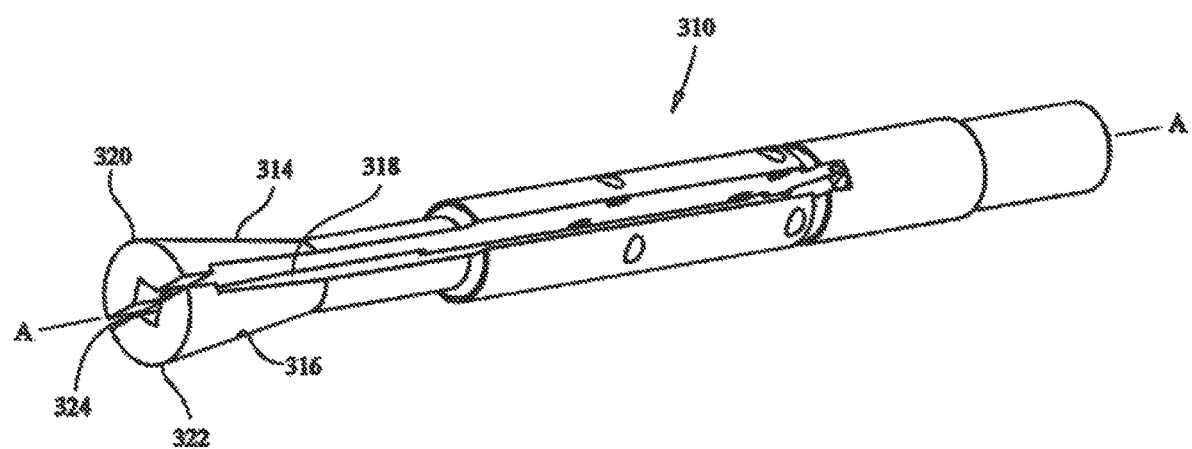
FIG. 27 depicts a front isometric view of the collet of the medical device of FIG. 17.

Referring to FIGS. 18 and 27, collet 310 is affixed to second end portion 312 of collet holder 208, opposite cable tensioner 216. Collet 310 defines a collet passage longitudinally aligned with the longitudinal passage of collet holder 208, along central longitudinal axis A-A. An end portion of collet 310 is bisected, forming first and second collet arms 314 and 316. Gap portion 318 is provided between first and second collet arms 314 and 316. Each of first and second collet arms 314 and 316 include force application end portions 320 and 322. force application end portions 320 and 322, combine to form bushing aperture 324 configured to received bushing 146 therein. Collet 310 is made of a semi-rigid material, such that first and second collet arms 314 and 316 can be moved from an open to closed position, closing gap 318 and bushing aperture 324 between force application end portions 320 and 322.

In use, tensioning mechanism 204 is used to tension cable 132. As discussed above, cable 132 can include single or multiple filaments. Cable 132 is inserted through medical device 200 along central longitudinal axis A-A, through collet 310, collet holder 208, and cable tensioner 216, positioning bushing in bushing aperture 324 and extending cable through cable aperture 222. To tension cable, winding knob 270 is rotated until a desired tension is achieved. Desired tension can be selected by setting thumb cap 300 to the desired tension marking.

Referring again to FIGS. 17 and 28, crimping mechanism 206 includes an outer tube 330 slideably positioned over collet holder 208. Outer tube 330 includes first end 332 operably connected to trigger 334 and second end 336 connected to collet closer 338. Trigger 334 is pivotally mounted in handle portion 202, such that trigger 334 can be actuated from first trigger position TR1 to second trigger position TR2. With additional reference to FIG. 32, locking mechanism 370 can be included, in accordance with one embodiment of the invention, which prevents trigger 334 from being accidentally actuated. Locking mechanism 370 is disengaged by rotating it away from handle, where locking mechanism 370 is secured to trigger with locking pawl 371.

Figure 28:
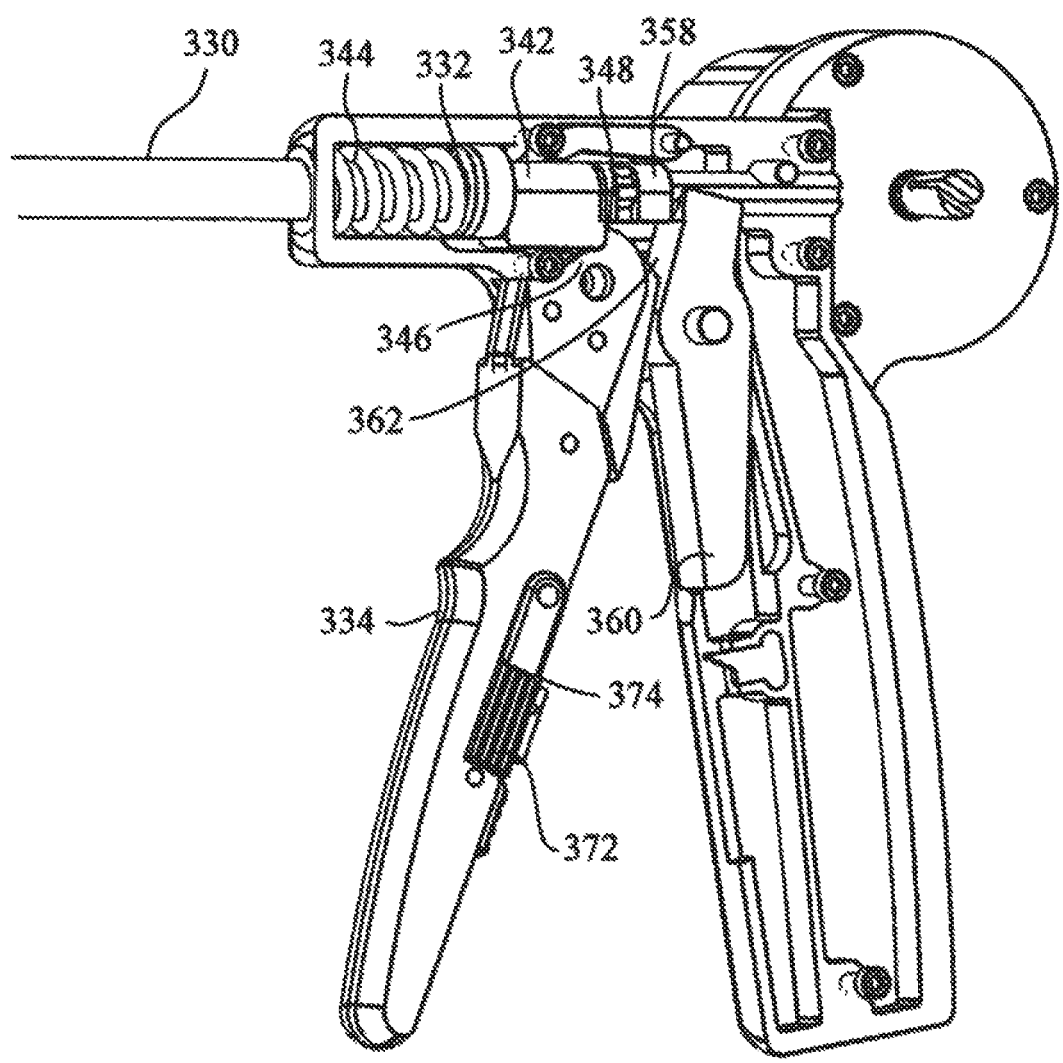
FIG. 28 depicts a partial sectional view of the crimping mechanism of the medical device of FIG. 17.
Figure 29:
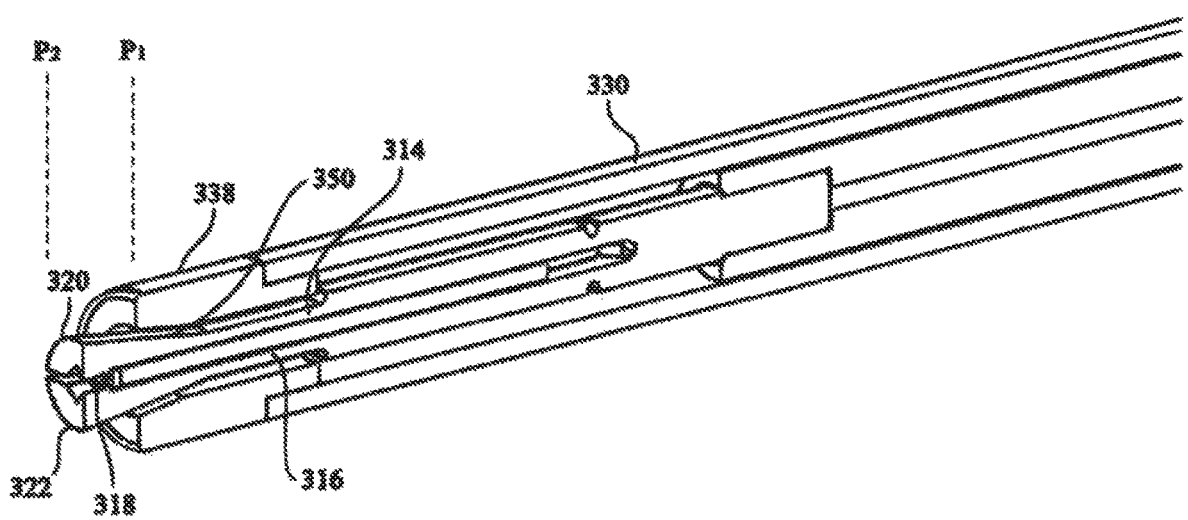
FIG. 29 depicts an partial sectional view of the crimping mechanism of the medical device of FIG. 17.

With reference to FIG. 28, operable connection between first end of outer tube 332 and trigger 334 includes an outer tube ferrule engagement member 342 slidably positioned about collet holder 208 and engaging first end 332 of outer tube 330. Tube bias member 344 is interposed between handle portion 202 and outer tube ferrule 332, such that tube bias member 344 biases outer tube ferrule 332 and outer tube 330 into a first tube position P1 (FIG. 29). An upper trigger portion 346 includes first edge 348, where first edge 348 engages outer tube ferrule engagement member 342 when trigger 334 is actuated from first trigger position TR1 to second trigger position TR2.

First edge 348 engagement of outer tube ferrule 332 moves outer tube ferrule 332 and outer tube 330 along collet holder 208 from a first tube position P1 to a second tube position P2. As trigger 334 is released, tube bias member 344 biases outer tube ferrule 332 and outer tube 33 from second tube position P2 to first tube position P1. Simultaneously, trigger 334 is moved to first trigger position TR1.

Referring to FIGS. 17 and 29, collet closer 338 is positioned on outer tube 330 proximal to the force application end portions 320 and 322 of first and second collet arms 314 and 316. As outer tube 330 is moved from first tube position P1 to second tube position P2, collet closer 338 is moved over force application end portions 320 and 322. Collet closer 338 includes inner tapered surfaces 350, such that inner tapered surfaces 350 applies compressive force to force application end portions 320 and 322 together as collet closer 338 is moved over force application end portions 320 and 322, thus closing gap 318 therebetween.

In use, trigger 334 is actuated from first trigger position TR1 to second trigger position TR2. Actuation of trigger 334 slides outer tube 330 along collet holder 208 from first tube position P1 to second tube position P2, moving collet closer 338 along force application end portions 320 and 322 of first and second collet arms 314 and 316. Inner tapered surfaces 350 of collet closer 330 apply compressive forces to first and second force application end portions 320 and 320, closing gap 318 and reducing bushing aperture 324 therebetween. Trigger 334 is released, allowing tube bias member 344 to bias outer tube 330 from second tube position P2 to first tube position P1, moving collet closer 338 away from force application end portions 320 and 322.

Figure 30:
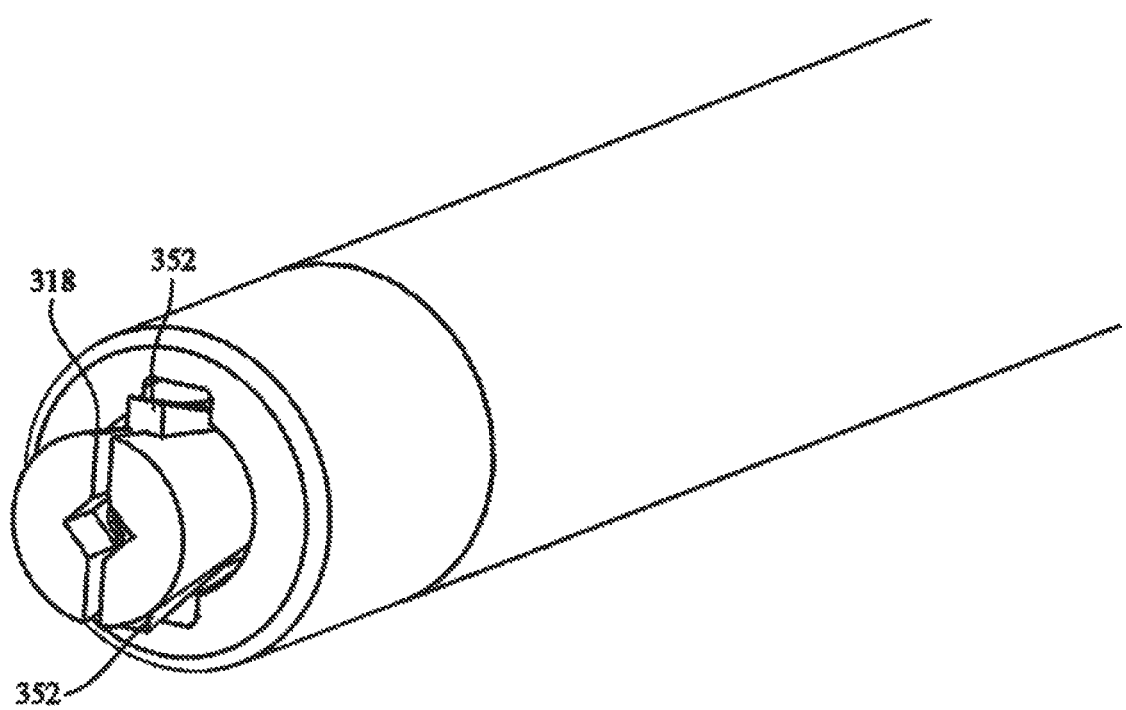
FIG. 30 depicts a partial isometric view showing the cutting mechanism of the medical device of FIG. 17.
Figure 31:
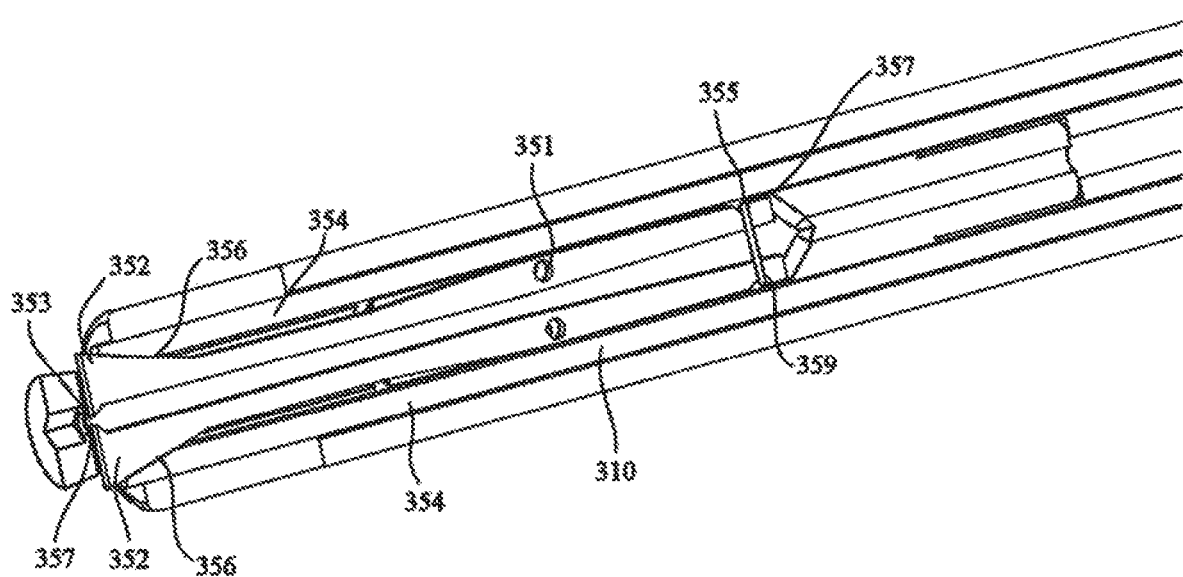
FIG. 31 depicts a partial sectional view showing the cutting mechanism of FIG. 30.

Collet aperture 324 is configured to receive a cable 110/132 as described herein. In general, collet aperture 324 can be configured to receive any fastener body. Examples of alternative collet aperture configurations may be found U.S. patent application Ser. No. 11/358,331, contents of which are hereby incorporated by reference Referring to FIGS. 30-31, crimping mechanism 206 can, in accordance with the invention, further include a cutting mechanism. In one embodiment, a cutting mechanism includes a pair of cut off cams 352 positioned in collet gap 318. Cut of cams 352 each include pin hole 351 such that a pin is inserted through collet 310 and each of cut of cams 352, pivotally connecting cut off cams 352 to collet 310. Cut off cams 352 each include cutting edges 353 for cutting cable. A pair of wedges 354 are slidingly positioned along and on opposite sides of collet 310 and collet holder 208. Each of wedges 354 include tapered ends 356 positioned proximal to cut off cams 352, such that when wedges are moved from first wedge position W1 to second wedge position W2, tapered ends 356 compress cut off cams 350 together, cutting cable 132. Biasing member 355 is positioned about the end of cut-off cams 357, biasing cutting edges 353 in an open position. End portions 357 can include notched section 359 for retaining biasing member 355 thereon. Biasing member 355 can be a circular nitinol spring, however any elastic member will due.

Figure 33:
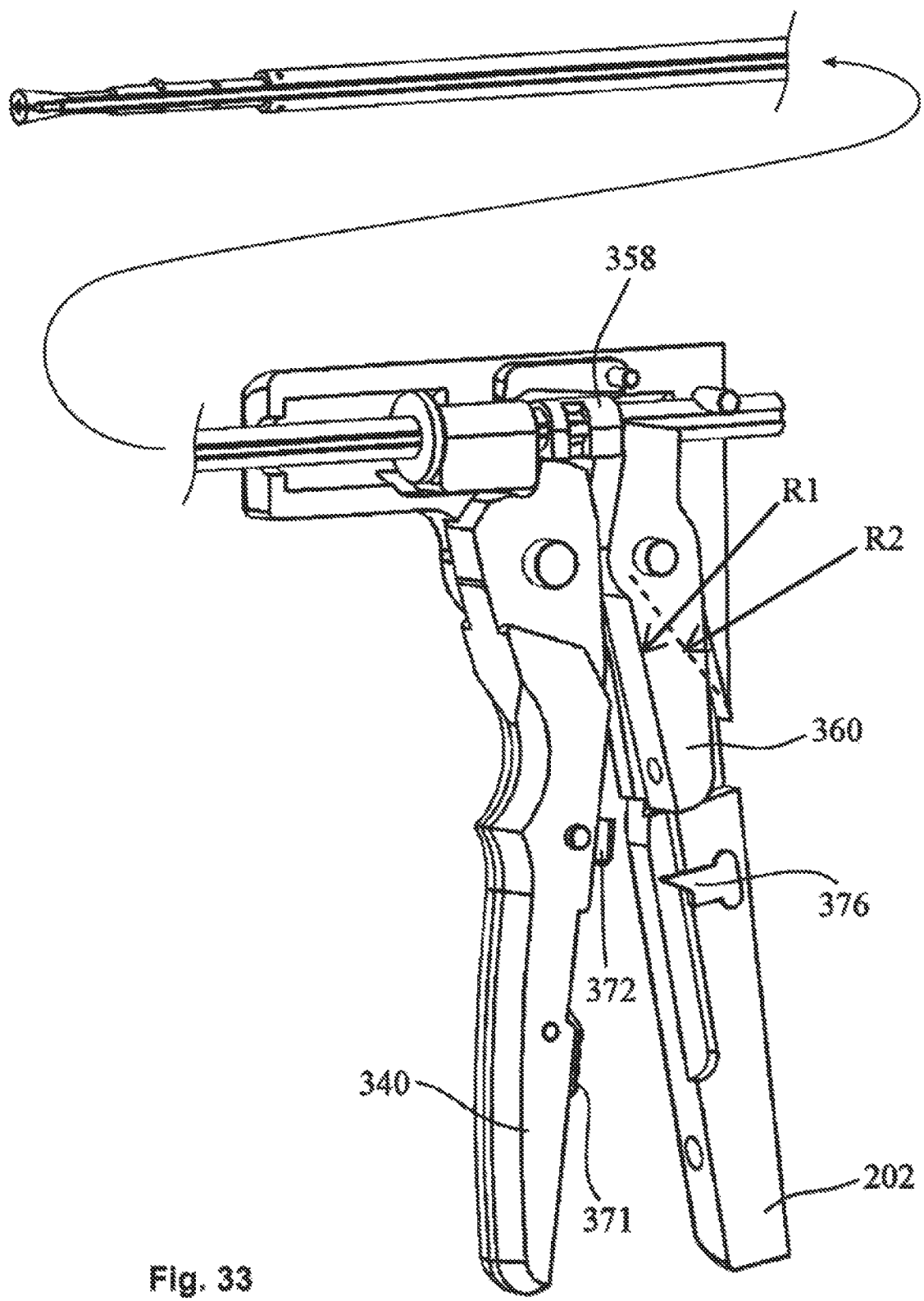
FIG. 33 depicts a partial isometric view showing the handle portion of the cutting mechanism.

With reference to FIG. 33, handle 202 further includes wedge pusher 358 slidingly positioned about collet holder 208, adjacent to second ends of wedges 354. Wedge pusher 358 is slidable from a first position to a second position, such that wedges 354 are moved from a first wedge position W1 to a second wedge position W2.

Rocker 360 is pivotally connected to handle 202, such that an actuation of rocker 360 from first rocker position R1 to second rocker position R2, slides wedge pusher 358 from first position to second position, moving wedges 354 from first wedge position W1 to second wedge position W2.

Figure 32:
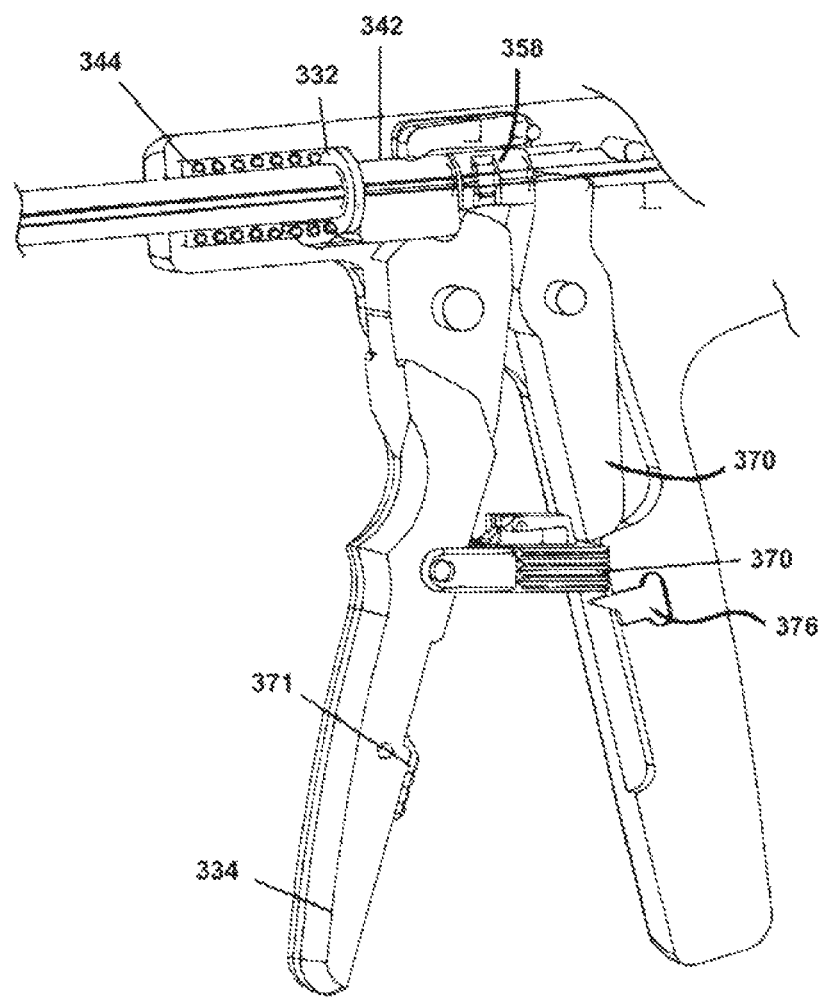
FIG. 32 depicts the locking mechanism of the medical device of FIG. 17.
Figure 34:
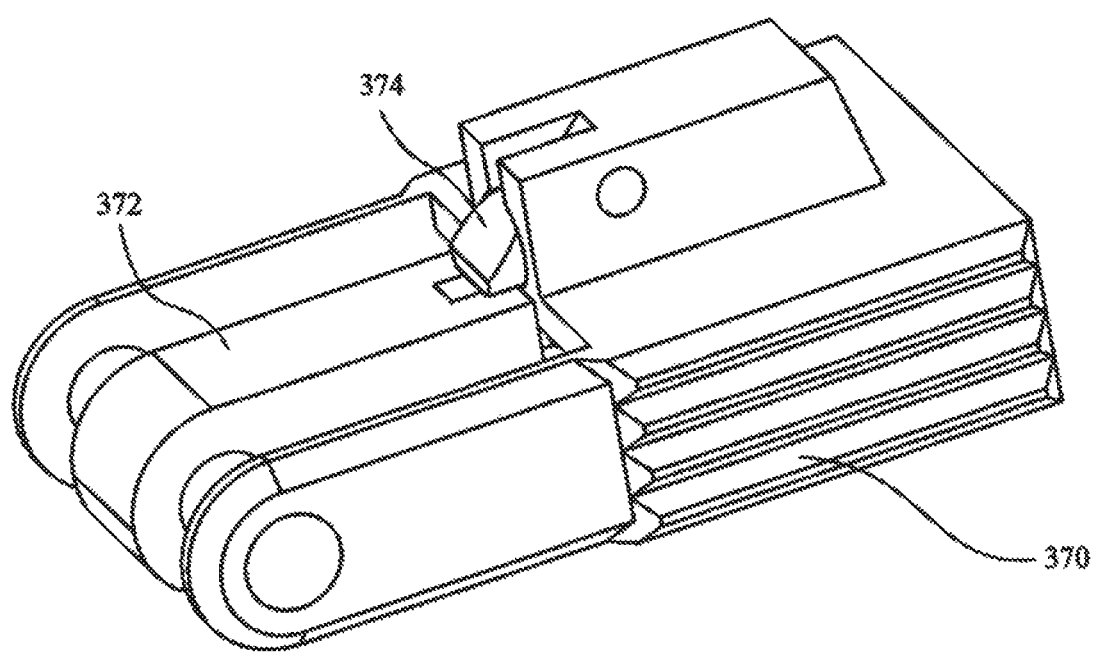
FIG. 34 depicts a safety lock of the medical device of FIGS. 17.

Referring to FIGS. 32-34, locking mechanism 370 includes rocker kicker 372 pivotally affixed therein. Rocker kicker 372 is biasedly connected to locking mechanism 370, being held in a closed position by pin 374. When trigger 334 is actuated from first trigger position TR1 to second trigger position TR2, release 376 engages pin 374, releasing rocker kicker 372.

When trigger 334 is released, trigger 334 is allowed to move from second trigger position TR2 to first trigger position TR1. To actuate cutting cams 352, trigger 334 is again moved from first trigger position TR1 to second trigger position TR2, such that rocker kicker 372 engages rocker 360, pivoting rocker 360 from first rocker position R1 to second rocker position R2. Rocker 360 slides wedge pusher 358 from first position to second position, moving wedges 354 from first wedge position W1 to second wedge position W2, such that, tapered ends 356 urge cut off cams 352 together, whereupon a cable 132 may be cut. Trigger 334 can then be released, releasing the crimped fastener 100.

Figure 35:
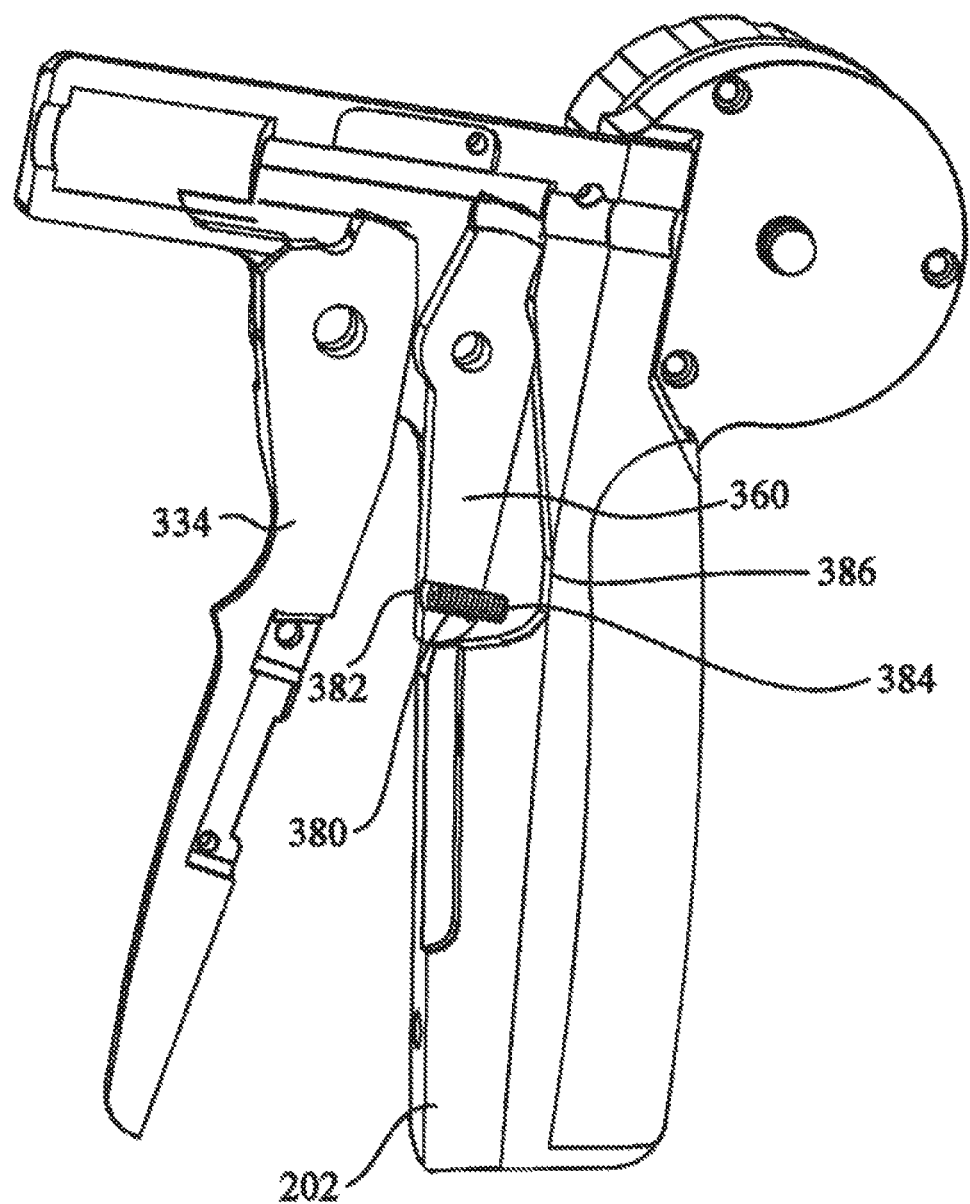
FIG. 35 depicts a stroke limiter of the cutting mechanism.

Referring to FIG. 35, a cutting mechanism in accordance with an embodiment of the invention further includes a stroke limiter to prevent overdriving of the cut of cams 352. The stroke limiter includes set screw 380 threadably positioned in threaded hole 382 through lower portion of rocker 360 set screw 380 is positioned such that back end of set screw 380 extends from rocker 360. When rocker 360 is actuated, the back end 384 of set screw contacts contacting surface 386 in handle 20, thus limiting travel of rocker 360 and wedges 354, to thereby limit compression of cutting edges 353. Set screw 380 can be adjusted to adjust maximal compression of cutting edges 353, thereby prevent overdriving of cut off cams 352.

In a method of use in accordance with the invention, cable 132 is passed through bone 104 and fracture 102, where first fastener 112a secures cable 132 on first side (fracture side) of bone and second fastener 112b is positioned about cable on second side of bone, opposite first fastener 112a. Bushing 146 is positioned onto cable 132 to secure second fastener 112a against second side of bone 104.

Cable 132 is inserted through medical device 200 along central longitudinal axis "A-A", through collet 310, collet holder 208, and cable tensioner 216, positioning bushing in bushing aperture 324 and extending cable through cable aperture 222. To tension cable, winding knob 270 is rotated until desired tension is reached. Prior to use, desired tension can be set by rotating thumb cap 300 to a tension indicated on cover plate 297.

Trigger 334 is actuated from first trigger position TR1 to second trigger position TR2. Actuation of trigger 334 slides outer tube 330 along collet holder 208 from first tube position P1 to second tube position P2, moving collet closer 338 about force application end portions 320 and 322 of first and second collet arms 314 and 316. Inner tapered surfaces 356 of collet closer 338 apply compressive forces to first and second force application end portions 320 and 322, compressing first and second force application end portions 320 and 322 about bushing 146 positioned in bushing aperture 324. Compressive forces crimp bushing about cable 132, securing bushing 146 to cable 132.

Simultaneously, actuation of trigger 334 results in rocker 360 engaging wedge pusher 358, sliding wedge pusher 358 and wedges 354 along collet holder 208. Tapered ends 356 of wedges 354 engage cut off cams 352, forcing cutting edge 353 into cable 132, cutting cable 132.

The components of the medical device 200 of the present invention are rigid members made of, for example, aluminum, stainless steel, polymeric, composite materials, or combinations thereof. The components are sufficiently rigid to transmit the necessary forces. It should be understood that any material of sufficient rigidity might be used. For example, some components can be made by injection molding. Generally, for injection molding, tool and die metal molds of the components are prepared. Hot, melted plastic material is injected into the molds. The plastic is allowed to cool, forming components. The components are removed from the molds and assembled.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such an instance, the device can be used as a positioning device for use in imaging devices, such as an MRI device. It is also contemplated that the system and medical device of the present invention may be disposable or may be sterilized after use and reused.

The methods and devices of the present invention may be used in conjunction with any surgical procedure of the body. The repair, reconstruction, augmentation, and securing of tissue or an implant may be performed in connection with surgery of a joint, bone, muscle, ligament, tendon, cartilage, capsule, organ, skin, nerve, vessel, or other body part. For example, tissue may be repaired, reconstructed, augmented, and secured following intervertebral disc surgery, knee surgery, hip surgery, organ transplant surgery, bariatric surgery, spinal surgery, anterior cruciate ligament (ACL) surgery, tendon-ligament surgery, rotator cuff surgery, capsule repair surgery, fractured bone surgery, pelvic fracture surgery, avulsion fragment surgery, hernia repair surgery, and surgery of an intrasubstance ligament tear, annulus fibrosis, fascia lata, flexor tendons, etc. In one particular application, an anastomosis is performed over a balloon and the methods and devices of the present invention are used to repair the vessel.

Also, tissue may be repaired after an implant has been inserted within the body. Such implant insertion procedures include, but are not limited to, partial or total knee replacement surgery, hip replacement surgery, bone fixation surgery, etc. The implant may be an organ, partial organ grafts, tissue graft material (autogenic, allogenic, xenogenic, or synthetic), collagen, a malleable implant like a sponge, mesh, bag/sac/pouch, collagen, or gelatin, or a rigid implant made of metal, polymer, composite, or ceramic. Other implants include biodegradable plates, porcine or bovine patches, metallic fasteners, compliant bearings for one or more compartments of the knee, nucleus pulposus prosthetic, stent, tissue graft, tissue scaffold, biodegradable collagen scaffold, and polymeric or other biocompatible scaffold. The scaffold may include fetal cells, stem cells, embryonal cells, enzymes, and proteins.

The present invention further provides flexible and rigid fixation of tissue. Both rigid and flexible fixation of tissue and/or an implant provides compression to enhance the healing process of the tissue. A fractured bone, for example, requires the bone to be realigned and rigidly stabilized over a period time for proper healing. Also, bones may be flexibly secured to provide flexible stabilization between two or more bones. Soft tissue, like muscles, ligaments, tendons, skin, etc., may be flexibly or rigidly fastened for proper healing. Flexible fixation and compression of tissue may function as a temporary strut to allow motion as the tissue heals. Furthermore, joints which include hard and soft tissue may require both rigid and flexible fixation to enhance healing and stabilize the range of motion of the joint. Flexible fixation and compression of tissue near a joint may provide motion in one or more desired planes. The fasteners described herein and incorporated by reference provide for both rigid and flexible fixation.

It is contemplated that the devices and methods of the present invention be applied using minimally invasive incisions and techniques to preserve muscles, tendons, ligaments, bones, nerves, and blood vessels. A small incision(s) may be made adjacent the damaged tissue area to be repaired, and a tube, delivery catheter, sheath, cannula, or expandable cannula may be used to perform the methods of the present invention. U.S. Pat. No. 5,320,611 entitled, Expandable Cannula Having Longitudinal Wire and Method of Use, discloses cannulas for surgical and medical use expandable along their entire lengths. The cannulas are inserted through tissue when in an unexpanded condition and with a small diameter. The cannulas are then expanded radially outwardly to give a full-size instrument passage. Expansion of the cannulas occurs against the viscoelastic resistance of the surrounding tissue. The expandable cannulas do not require a full depth incision, or at most require only a needle-size entrance opening.

Also, U.S. Pat. Nos. 5,674,240; 5,961,499; and 6,338,730 disclose cannulas for surgical and medical use expandable along their entire lengths. The cannula has a pointed end portion and includes wires having cores which are enclosed by jackets. The jackets are integrally formed as one piece with a sheath of the cannula. The cannula may be expanded by inserting members or by fluid pressure. The cannula is advantageously utilized to expand a vessel, such as a blood vessel. An expandable chamber may be provided at the distal end of the cannula. The above mentioned patents are hereby incorporated by reference.

In addition to using a cannula with the methods of the present invention, an introducer may be utilized to position fasteners at a specific location within the body. U.S. Pat. No. 5,948,002 entitled Apparatus and Method for Use in Positioning a Suture Anchor, discloses devices for controlling the placement depth of a fastener. Also, U.S. patent application Ser. No. 10/102,413 discloses methods of securing body tissue with a robotic mechanism. The above-mentioned patent and application are hereby incorporated by reference. Another introducer or cannula which may be used with the present invention is the VERSASTEP® System by TYCO® Healthcare.

The present invention may also be utilized with minimally invasive surgery techniques disclosed in U.S. patent application Ser. No. 10/191,751 and U.S. Pat. Nos. 6,702,821 and 6,770,078. These patent documents disclose, inter alia, apparatus and methods for minimally invasive joint replacement. The femoral, tibial, and/or patellar components of a knee replacement may be fastened or locked to each other and to adjacent tissue using fasteners disclosed herein and incorporated by reference. Furthermore, the methods and devices of the present invention may be utilized for repairing, reconstructing, augmenting, and securing tissue or implants during and "on the way out" of a knee replacement procedure. For example, the anterior cruciate ligament and other ligaments may be repaired or reconstructed; quadriceps mechanisms and other muscles may be repaired. The patent documents mentioned above are hereby incorporated by reference.

In addition, intramedullary fracture fixation and comminuted fracture fixation may be achieved with the devices and methods of the present invention. For example, a plate or rod may be positioned within or against the fractured bone. A fastener may be driven through or about the bone and locked onto the plate, rod, or another fastener.

It is further contemplated that the present invention may be used in conjunction with the devices and methods disclosed in U.S. Pat. No. 5,329,846 entitled, Tissue Press and System, and U.S. Pat. No. 5,269,785 entitled, Apparatus and Method for Tissue Removal. For example, an implant secured within the body using the present invention may include tissue harvested, configured, and implanted as described in the patents. The above-mentioned patents are hereby incorporated by reference.

Furthermore, it is contemplated that the methods of the present invention may be performed under indirect visualization, such as endoscopic guidance, computer assisted navigation, magnetic resonance imaging, CT scan, ultrasound, fluoroscopy, X-ray, or other suitable visualization technique. The implants, fasteners, fastener assemblies, and sutures of the present invention may include a radiopaque material for enhancing indirect visualization. The use of these visualization means along with minimally invasive surgery techniques permits physicians to accurately and rapidly repair, reconstruct, augment, and secure tissue or an implant within the body. U.S. Pat. Nos. 5,329,924; 5,349,956; and 5,542,423 disclose apparatus and methods for use in medical imaging. Also, the present invention may be performed using robotics, such as haptic arms or similar apparatus. The above-mentioned patents are hereby incorporated by reference.

All references cited herein are expressly incorporated by reference in their entirety.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention. Therefore, it will be understood that the appended claims are intended to cover all such modifications and embodiments which come within the spirit and scope of the present invention.

What is claimed is:

1. A tensioning device comprising:
   a cannulated tube having opposite proximal and distal ends, and a longitudinal passage configured to enable an elongate member to be passed through the longitudinal passage;
   a handle attached to the proximal end of the cannulated tube; and
   a rotatable shaft incorporated into the handle having an axis extending generally transverse to the longitudinal passage and having an open ended slot, wherein the rotatable shaft is rotatably coupled to the cannulated tube and configured to be selectively rotatable about its axis relative to the cannulated tube,
   wherein the slot in the rotatable shaft is configured to receive the elongate member such that the elongate member wraps around the rotatable shaft as the rotatable shaft rotates about its axis to apply tension to the elongate member.

2. The tensioning device of claim 1, further comprising a locking assembly, wherein the locking assembly is configured to at least one of maintain the tension applied to the elongate member and prevent reversal of the rotatable shaft.

3. The tensioning device of claim 1, wherein the elongate member is comprised at least in part of polyethylene.

4. The tensioning device of claim 1, wherein the elongate member is at least one of a suture, a thread, a cable, and a tape; and at least one of threadlike, multifilament, braided, and interlaced.

5. The tensioning device of claim 1, wherein the device is configured to be operated with a surgical robotic mechanism.

6. The tensioning device of claim 1, further comprising a tension limiting mechanism configured to restrict tensioning of the elongate member beyond a predetermined tension limit.

7. The tensioning device of claim 1, wherein the tensioning device is configured to secure a graft using the elongate member during anterior cruciate ligament surgery.

8. The tensioning device of claim 1, further comprising a knob attached to the rotatable shaft.

9. The tensioning device of claim 1, further comprising a tension indicator configured to indicate the tension being applied to the elongate member.

10. The tensioning device of claim 9, wherein the tension indicator displays the tension measured by at least one of a sensor and a spring.

11. The tensioning device of claim 1, further comprising a crimping mechanism positionable in the distal end of the cannulated tube, the crimping mechanism having at least one force application member configured to apply at least one external compressive force to reduce the aperture of a malleable fastener positionable in the crimping mechanism to secure the fastener to the elongate member.

12. The tensioning device of claim 1, wherein the elongate member is configured to be secured to an anterior cruciate ligament and the tension applied to the elongate member is configured to tension the anterior cruciate ligament.

13. The tensioning device of claim 1, wherein the elongate member is secured to an anterior cruciate ligament graft and the tension applied to the elongate member tensions the anterior cruciate ligament graft.

14. The tensioning device of claim 1, wherein the elongate member is configured to be secured to a ligament and the tension applied to the elongate member is configured to tension the ligament.

15. The tensioning device of claim 1, wherein the elongate member is configured to be secured to a rotator cuff tendon and the tension applied to the elongate member is configured to tension the rotator cuff tendon.

16. The tensioning device of claim 1, wherein the elongate member is configured to be secured to a tendon and the tension applied to the elongate member is configured to tension the tendon.

17. The tensioning device of claim 1, wherein the elongate member is secured to a graft and the tension applied to the elongate member tensions the graft.

18. The tensioning device of claim 1, wherein the elongate member is secured to at least one of a fastener and an anchor and the tension applied to the elongate member applies a tension to the at least one fastener and anchor.

19. The tensioning device of claim 1, wherein the tensioning device is configured to apply a tension to the elongate member secured between at least one of a first fastener and a first anchor and at least one of a second fastener and a second anchor.

20. The tensioning device of claim 1, further comprising a cutting mechanism configured to remove an excess of the elongate member.

* * * * *